United States Patent [19]

Murakami et al.

[11] 4,068,074
[45] Jan. 10, 1978

[54] CEPHALOSPORIN DERIVATIVES HAVING AT THE 3-POSITION OF THE CEPHEM RING A HETEROCYCLIC THIOMETHYL GROUP WITH A CARBOXY OR SULFO GROUP AND AT THE 7-POSITION OF THE CEPHEM RING AN α-HETEROCYLIC ACYLAMINOPHENYL-ACETAMIDE GROUP

[75] Inventors: Masuo Murakami, Tokyo; Ichiro Isaka, Hoya; Norio Kawahara, Ageo; Masaru Iwanami, Yokohama; Masaharu Fujimoto, Tokyo; Tetsuya Maeda, Urawa; Tadao Shibanuma, Asaki; Yoshinobu Nagano, Niiza, all of Japan

[73] Assignee: Yamanouchi Pharmaceutical Co., Ltd., Tokyo, Japan

[21] Appl. No.: 695,085

[22] Filed: June 11, 1976

Related U.S. Application Data

[63] Continuation-in-part of Ser. No. 562,884, March 28, 1975, abandoned.

[30] Foreign Application Priority Data

Apr. 5, 1974 Japan .................................. 49-38545
Apr. 15, 1974 Japan .................................. 49-41884

[51] Int. Cl.$^2$ ............................................ C07D 501/36
[52] U.S. Cl. ...................................... 544/27; 424/246
[58] Field of Search .................................... 260/243 C

[56] References Cited

U.S. PATENT DOCUMENTS 3,989,687  11/1976  Bambury et al. ................ 260/243 C

OTHER PUBLICATIONS

Chemical Abstracts, vol. 81, 120651g (1974).

*Primary Examiner*—Nicholas S. Rizzo
*Attorney, Agent, or Firm*—Burgess, Ryan and Wayne

[57] ABSTRACT

A novel cephalosporin derivative having at the 3-position of the cephem ring a heterocyclic thiomethyl group having a carboxy group or a sulfo group and at the 7-position of the cephem ring, an α-heterocyclic acylaminophenylacetamide group. The compounds of this invention have excellent antibacterial activity against Pseudomonas and Proteus strains of bacteria.

15 Claims, No Drawings

CEPHALOSPORIN DERIVATIVES HAVING AT THE 3-POSITION OF THE CEPHEM RING A HETEROCYCLIC THIOMETHYL GROUP WITH A CARBOXY OR SULFO GROUP AND AT THE 7-POSITION OF THE CEPHEM RING AN α-HETEROCYLIC ACYLAMINOPHENYL-ACETAMIDE GROUP

The present application is a continuation-in-part of application Ser. No. 562,884, filed Mar. 28, 1975, and now abandoned.

DETAILED DESCRIPTION OF THE INVENTION

The present invention relates to novel cephalosporin derivatives. More particularly, the invention relates to novel cephalosporin derivatives represented by the formula

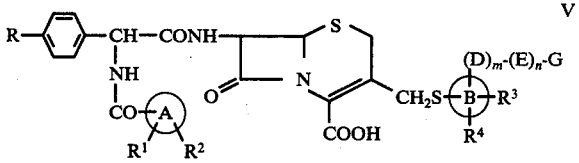

wherein R represents a hydrogen atom or a hydroxy group; (A) represents a 5- or 6-membered ring having 1-2 nitrogen atoms, a quinoline ring, or a thiopyran ring; $R^1$ and $R^2$, which may be the same or different, each represents a hydrogen atom, a hydroxy group, a lower alkyl group, a lower alkoxy group, a lower alkylthio group, or an oxo group; (B) represents a 6-membered ring having 1-4 nitrogen atoms and/or 0-1 sulfur atoms, a 6-membered ring having 2 nitrogen atoms, or a 1,2,4-triazole[3,4-b]-1,3,4-thiadiazole ring when $R_3$ and $R_4$ are present, which may be the same or different, each represents a hydrogen atom, an oxo group, a lower alkyl group, or an amino group; D represents a sulfur atom or a -NHCO- group; E represents an alkylene group or a phenylene group; G represents a carboxy group or a sulfo group; $n$ is 0 or 1 when $m$ is 0; and $n$ is 1 when $m$ is 1, and the nontoxic salts thereof.

Typically the present invention relates to these cephalosporins V wherein R is hydrogen or hydroxy; (A) is an aromatic heterocyclic ring of 6 members having 1 or 2 nitrogen atoms, quinoline or thipyran; $R^1$ and $R^2$ which may be the same or different are each hydrogen, hydroxy, lower alkyl, lower alkoxy, lower alkylthio, or oxo; (B) is thiazole, thiadiazole, tetrazole, pyrimidine, pyridazine or 1,2,4-triazolo[3,4-b]-1,3,4-thiadiazole; $R^3$ and $R^4$ when they are present may be the same or different are hydrogen, amino, oxo, or lower alkyl D is a sulfur atom; E is alkylene; G is carboxy or sulfo; $n$ is 0 or 1 when $m$ is 0; and $n$ is 1 when $m$ is 1 and the pharmaceutically acceptable salts thereof.

As the compounds of this invention show antibacterial activities against a wide range of gram positive bacteria and gram negative bacteria and show, in particular, excellent antibacterial activities against Pseudomonas and Proteus strains of bacteria, they can be administered to human beings and animals as agents for treating various diseases caused by these bacteria.

Heretofore, cephalosporin derivatives effective against Pseudomonas strains were not known but by the discovery of the novel cephalosporin derivatives of this invention, it becomes possible to treat the diseases caused by these strains.

Examples of the 5- or 6-membered ring having 1-2 nitrogen atoms shown by ring (A) in this invention are a pyrrole ring, an imidazole ring, a pyrazole ring, a pyridine ring, a pyrimidine ring, a pyridazine ring, a pyrazine ring, etc. These rings may be partially saturated. Examples of the 5-membered ring having 1-4 nitrogen atoms and/or 0-1 sulfur atom shown by ring (B) are a pyrrole ring, an imidazole ring, a pyrazole ring, a triazole ring, a tetrazole ring, a thizaole ring, an isothiazole ring, a 1,2,4-thiadiazole ring, a 1,3,4-thiadiazole ring, etc. Also, examples of the 6-membered ring having 2-nitrogen atoms are a pyrimidine ring, a pyrazine ring, a pyridazine ring, etc. These rings may be partially saturated. Example of the lower alkyl group in $R^1$–$R^4$ or the lower alkyl group forming a lower alkoxy group or a lower alkylthio group in $R^1$–$R^4$ are a methyl group, an ethyl group, a propyl group, an isopropyl group, a butyl group, etc. Furthermore, examples of an alkylene group in substituent E are, for example, a methylene group, an ethylene group, a trimethylene group, an isopropylidene group, an ethylidene group, a propylene group, etc.

The compounds of this invention shown by general formula V can be prepared by, for example, reacting a compound represented by the general formula I

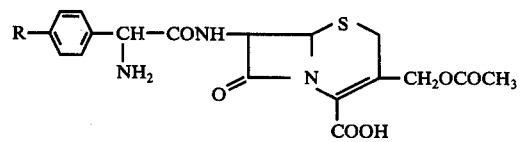

wherein R has the same meaning as in general formula V and the heterocyclic carboxylic acid is represented by the general formula II

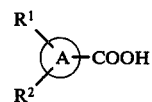

wherein (A), $R^1$, and $R^2$ have the same meaning as in general formula V or a reactive derivative thereof to produce a compound shown by general formula III:

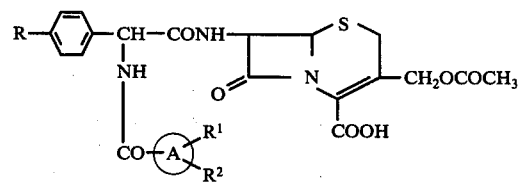

and then reacting the product with the mercapto-substituted hetero-cyclic ring compound represented by the general formula IV

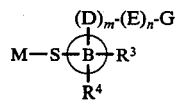

wherein M represents a hydrogen atom or an alkali metal atom and $R^3$, $R^4$, B, D, E, G, $m$ and $n$ have the same meaning as in general formula V or, more precisely, a heterocyclic compound substituted by a carboxyl group or a sulfo group, and a mercapto group.

The reactions are illustrated by the following reaction scheme:

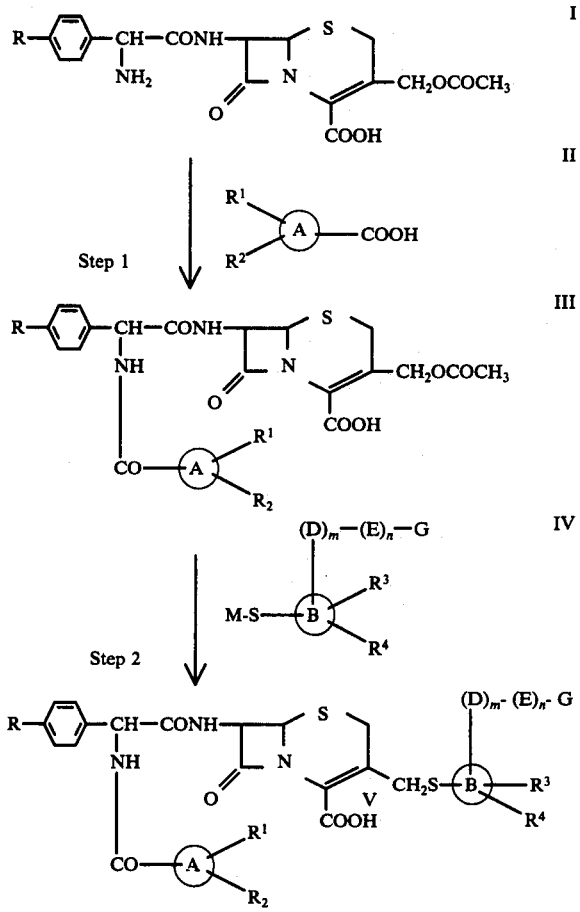

wherein Ⓐ, Ⓑ, D, E, G, R, R¹, R², R³, R⁴, m and n have the same meaning as in the above formulae.

The reaction of step 1 is carried out by reacting the compound of formula I and an almost equimolar or excessive amount of the compound of formula II or the reactive derivative thereof.

When the compound of formula II is used in the free state or the salt thereof, the reaction is carried out preferably in the presence of a condensing agent such as N, N-dicyclohexylcarbodiimide; a phosphoric acid trialkyl ester, e.g., triethyl phosphate; a phosphorus oxyhalide, e.g., phosphorus oxychloride; a phosphorus trihalide, e.g., phosphorus trichloride; a thionyl halide, e.g., thionyl chloride; an oxazolyl chloride; and the like.

Examples of the preferred reactive derivatives of the compounds of formula II are, for example, acid halides; acid azides; acid anhydrides; mixed acid anhydrides such as an alkylcarboxylic acid mixed acid anhydride, an alkyl phosphoric acid mixed acid anhydride, a dialkyl phosphorus acid mixed acid anhydride, a sulfuric acid mixed acid anhydride, etc., as well as an active amide with imidazole, an active ester, such as p-nitrophenyl ester, etc.

When an alkylcarboxylic acid mixed acid anhydride, an acid halide, etc. is used as the reactive derivative of the compound of formula II, the reaction is ordinarily carried out in an organic solvent such as acetone, tetrahydrofuran, dimethyl formamide, chloroform, dichlormethane, hexamethyl phosphoramide (hexametapol), etc., or a mixed solvent thereof in the presence of a base such as triethylamine, dimethylaniline, etc., under cooling or at room temperature.

The compound of formula III formed is usually isolated and purified by ordinary chemical procedure such as extraction, recrystallization, etc., and as the case may be, the reaction mixture containing the compound of formula III is applicable for the reaction with the compound of formula IV without further isolation or purification.

The reaction of step 2 is carried out by reacting the compound of formula III and an almost equimolar or excessive amount of the compound of formula IV. The reaction is ordinarily carried out in an aqueous solution, in an inert organic solvent such as acetone, ether, chloroform, nitrobenzene, dimethylsulfoxide, dimethylformamide, methanol, ethanol, etc., or a mixture thereof. The reaction is also carried out in a neutral state or in a slightly alkaline state and in the case of using the compound of formula IV wherein M is a hydrogen atom, the reaction is carried out in the presence of a basic material such as, for example, an alkali metal hydroxide, an alkali metal carbonate, triethylamine, etc. The reaction may be carried out at room temperature but there is no particular limitation about the reaction temperature and, for example, the reaction system may be heated to a boiling point of the solvent used in the reaction.

The order of the reaction of step 1 and step 2 may be reversed. The object product of formula V may be isolated and purified by ordinary chemical operations such as extraction, recrystallization, etc. Furthermore, the compound of formula V can be converted in to a pharmaceutically acceptable salt thereof e.g., inorganic salts thereof, such as an alkali metal salt, an ammonium salt, etc., and organic salts thereof, such as salts with triethylamine, diethanolamine, lysine, ornithine, etc.

There are many compounds of formula V thus prepared but in the preferred compound of formula V, ring Ⓐ is a pyridine ring; substituent R is a hydrogen atom; R' is a hydroxy group or an oxo group; ring Ⓑ is a thiazole ring, a thiadiazole ring, or a tetrazole ring; D is a sulfur atom; E is an alkylene group having 1-2 carbon atoms; G is a carboxy group; m is 0 or 1; and n is 1.

In a more preferable embodiment, the compound of formula V of this invention, ring Ⓐ has a hydroxy group or an oxo group at the 4-position thereof; the alkylene group is a methylene group; G is a carboxy group; D is a sulfur atom; the thiadiazole ring of ring Ⓑ is a 1,2,4-thiadiazole ring or 1,3,4-thiadiazole ring; and m is 1.

Suitable examples of the compounds of formula V are as follows:

7-[D-α-(4-Hydroxynicotinoylamido)-α-phenylacetamido]-3-(5-carboxymethylthio)-1,3,4-thiadiazol-2-yl)thiomethyl-Δ³-cephem-4-carboxylic acid, 7-[D-α-(4-Hydroxynicotinoylamido)-α-phenylacetamido]-3-(3-carboxymethylthio-1,2,4-thiadiazol-5-yl)thiomethyl-Δ³-cephem-4-carboxylic acid, 7-[D-α-(4-Hydroxynicotinoylamido)-α-phenylacetamido]-3-(4-methyl-5-carboxythiazol-2-yl)thiomethyl-Δ³-cephem-4-carboxylic acid, 7-[D-α-(4-Hydroxynicotinoylamido)-α-phenylacetamido]-3-(1-carboxymethyl-1H-tetazol-5-yl)thiomethyl-Δ³-cephem-4-carboxylic acid, 7-[D-α-(4-Hydroxynicotinoylamido)-α-phenylacetamido]-3-(5-carboxymethyl-4-methyl-thiazol-2-yl)thiomethyl-Δ³-cephem-4-carboxylic acid, 7-[D-α-(4-Hydroxynicotinoylamido)-α-phenylacetamido]-3-(5-carboxymethyl-1,3,4-thiadiazol-2-yl)thiomethyl-Δ³-cephem-4-carboxylic acid, 7-[D-α-(4-Hydroxy 3-methylpyridin-5-ylcarboxamido)-α-phenylacetamido]-3-(5-carboxymethylthio-1,3,4-thiadiazol-2-yl)thiomethyl-Δ³-cephem-4-carboxylic acid, 7-[D-α-(4-Hydroxy-6-methylnicotinoylamido)-α-phenylacetamido]-3-(5-carboxymethylthio-1,3,4-thiadiazol-2-yl)thiomethyl-Δ³-cepham-4-carboxylic acid, and the like.

Now, for illustrating the excellent pharmacological effects of the compounds of this invention, the values of MIC (γ/ml.) of the compounds against various bacteria are shown in Table 1, in which the compounds of this invention used are shown by example numbers.

TABLE I

| Known compound | Bacterial (1) | (2) | (3) | (4) | (5) | (6) | (7) | (8) | MIC (γ/ml) (9) | (10) | (11) | (12) | (13) | (14) | (15) | (16) | (17) | (18) |
|---|---|---|---|---|---|---|---|---|---|---|---|---|---|---|---|---|---|---|
| Cephalexin | 30 | 30 | — | >100 | — | — | 10 | 3 | 6.25 | 6.25 | 6.25 | 6.25 | 0.78 | 0.78 | 1.56 | 1.56 | 6.25 | 12.5 |
| Cephaloglycin | 25 | 100 | 100 | >100 | >100 | >100 | 100 | 25 | 3 | 3 | 3 | 10 | 1 | 0.3 | 0.3 | 1 | 3 | 3 |
| Cephazolin | — | 25 | 6.25 | >100 | >100 | — | 1.56 | 1.56 | 1.56 | 1.56 | 1.56 | 1.56 | — | 0.19 | — | 0.19 | 0.78 | 1.56 |
| Cephalotin | 3.13 | 12.5 | — | >100 | >100 | >100 | 3.13 | 0.78 | 1.56 | 0.39 | 6.25 | 6.25 | — | <0.09 | 0.19 | 0.19 | 0.39 | 0.39 |
| Compound of Ex. 1 | 0.19 | 0.19 | 0.78 | 25 | 50 | 25 | 25 | 6.25 | 1.56 | 0.78 | 6.25 | 25 | 0.78 | 0.39 | 3.13 | 0.78 | 3.13 | 6.25 |
| 4 | <0.09 | 0.19 | 0.39 | 12.5 | 6.25 | 6.25 | 3.13 | 3.13 | 1.56 | 0.39 | 0.78 | 3.13 | 0.19 | 0.19 | 3.13 | 0.78 | 3.13 | 6.25 |
| 5 | <0.09 | 0.19 | 0.78 | 12.5 | 6.25 | 6.25 | 6.25 | 6.25 | 1.56 | 0.39 | 1.56 | 6.25 | 0.78 | 0.39 | 3.13 | 1.56 | 6.25 | 6.25 |
| 6 | <0.09 | <0.09 | 0.39 | 12.5 | 12.5 | 6.25 | 3.13 | 6.25 | 1.56 | 0.19 | 0.78 | 3.13 | 0.39 | 0.39 | 6.25 | 0.78 | 6.25 | 12.5 |
| 9 | <0.09 | 0.39 | 0.19 | 25 | 50 | 12.5 | 3.13 | 3.13 | 1.56 | 0.39 | 1.56 | 3.13 | 0.39 | 0.19 | 3.13 | 0.39 | 3.13 | 6.25 |
| 10 | 0.39 | 6.25 | 0.56 | 25 | 12.5 | 12.5 | 6.25 | 3.13 | 1.56 | 0.39 | 6.25 | 6.25 | 0.39 | 0.39 | 6.25 | 0.39 | 3.13 | 3.13 |
| 11 | 0.19 | 0.19 | 0.39 | 25 | 50 | 25 | 25 | 3.13 | 1.56 | 0.19 | 1.56 | 3.13 | 0.39 | 0.39 | 6.25 | 0.78 | 3.13 | 6.25 |
| 12 | <0.09 | 0.78 | 0.39 | 12.5 | 6.25 | 12.5 | 6.25 | 0.39 | 0.78 | 0.39 | 1.56 | 3.13 | 0.39 | 0.39 | 6.25 | 0.78 | 3.13 | 6.25 |
| 13 | 0.19 | 0.39 | 0.19 | 25 | 6.25 | 12.5 | 3.13 | 3.13 | 1.56 | 0.78 | 1.56 | 3.13 | 0.39 | 0.39 | 3.13 | 0.78 | 3.13 | 6.25 |
| 14 | 0.19 | 0.78 | <0.09 | 25 | 6.25 | 25 | 6.25 | 3.13 | 3.13 | 0.78 | 1.56 | 3.13 | 0.39 | 0.19 | 6.25 | 0.19 | 6.25 | 12.5 |
| 15 | 0.19 | 0.39 | 0.19 | 25 | 12.5 | 12.5 | 6.25 | 0.39 | 3.13 | 0.19 | 3.13 | 3.13 | 0.39 | 0.39 | 6.25 | 0.78 | 6.25 | 12.5 |
| 16 | <0.09 | <0.09 | <0.09 | 25 | 6.25 | 12.5 | 6.25 | 6.25 | 3.13 | 0.78 | 1.56 | 3.13 | 0.39 | 0.19 | 3.13 | 0.19 | 6.25 | 6.25 |
| 17 | — | <0.09 | 0.19 | — | 25 | 25 | 12.5 | 12.5 | 3.13 | 1.56 | 3.13 | 6.25 | 1.56 | 0.39 | 3.13 | 0.78 | 6.25 | 6.25 |
| 18 | — | 1.56 | 0.78 | — | 50 | 50 | 12.5 | 6.25 | 3.13 | 0.39 | 3.13 | 6.25 | 0.39 | 0.39 | 6.25 | 0.19 | 6.25 | 12.5 |
| 19 | — | 6.25 | 0.39 | — | 25 | 25 | 12.5 | 25 | 12.5 | 1.56 | 12.5 | 25 | 1.56 | 0.39 | 25 | 1.56 | 12.5 | 12.5 |
| 20 | — | 6.25 | 0.39 | — | 50 | 50 | 3.13 | 6.25 | 1.56 | 0.39 | 0.78 | 12.5 | 0.39 | 0.39 | 3.13 | 0.78 | 6.25 | 6.25 |
| 21 | <0.09 | 0.19 | 0.39 | 12.5 | 12.5 | 12.5 | 3.13 | 6.25 | 1.56 | 0.39 | 1.56 | 3.13 | 0.39 | 0.39 | 3.13 | 0.39 | 6.25 | 6.25 |
| 22 | 0.19 | 1.56 | 0.19 | 25 | 6.25 | 12.5 | 3.13 | 3.13 | 1.56 | 0.78 | 1.56 | 3.13 | 0.39 | 0.78 | 6.25 | 1.56 | 6.25 | 12.5 |
| 23 | <0.09 | <0.09 | 0.39 | 25 | 6.25 | 25 | 3.13 | 3.13 | 1.56 | 0.39 | 1.56 | 3.13 | 0.39 | 0.78 | 6.25 | 0.78 | 6.25 | 12.5 |
| 24 | <0.09 | 1.56 | 0.39 | — | 12.5 | 25 | 6.25 | 6.25 | 1.56 | 1.56 | 1.56 | 3.13 | 1.56 | 0.39 | 6.25 | 0.39 | 6.25 | 12.5 |
| 25 | <0.09 | <0.09 | 0.19 | — | 12.5 | 25 | 3.13 | 6.25 | 1.56 | 0.39 | 1.56 | 3.13 | 0.39 | 0.39 | 3.13 | 0.39 | 3.13 | 6.25 |
| 26 | 0.19 | 1.56 | 0.78 | 12.5 | 6.25 | 25 | 3.13 | 0.39 | 6.25 | 0.78 | 1.56 | 3.13 | 0.78 | 0.78 | 3.13 | 0.78 | 6.25 | 6.25 |
| 27 | <0.09 | 0.39 | 0.39 | 25 | 6.25 | 25 | 1.56 | 1.56 | 0.78 | 1.56 | 0.78 | 6.25 | 1.56 | 0.78 | 6.25 | 1.56 | 6.25 | 12.5 |
| 28 | <0.09 | 0.78 | 6.25 | — | 25 | 25 | 3.13 | 20 | 6.25 | 0.78 | 3.13 | 3.13 | 0.78 | 0.78 | 12.5 | 1.56 | 12.5 | 25 |
| 29 | <0.09 | 12.5 | 6.25 | 12.5 | 25 | 50 | 12.5 | 50 | 12.5 | 12.5 | 12.5 | 25 | 1.56 | 12.5 | 25 | 12.5 | 12.5 | 100 |
| 30 | <0.09 | 12.5 | 0.78 | 25 | 6.25 | 25 | 3.13 | 6.25 | 1.56 | 0.78 | 0.78 | 12.5 | 0.78 | 0.78 | 6.25 | 1.56 | 6.25 | 12.5 |
| 31 | — | 1.56 | 0.39 | 50 | 50 | 50 | 6.25 | 12.5 | 6.25 | 0.39 | 6.25 | 3.13 | 0.39 | 0.39 | 12.5 | 0.39 | 3.13 | 25 |
| 32 | <0.09 | 12.5 | 0.78 | 25 | 25 | 50 | 3.13 | 12.5 | 0.39 | 0.78 | 0.78 | 3.13 | 0.78 | 0.39 | 3.13 | 1.56 | 3.13 | 6.25 |
| 33 | <0.09 | 3.13 | 0.39 | — | 50 | 25 | 1.56 | 25 | 1.56 | 1.56 | 3.13 | 3.13 | 0.78 | 0.78 | 3.13 | 3.13 | 12.5 | 6.25 |
| 34 | <0.09 | 0.78 | 0.39 | — | 25 | 25 | 6.25 | 12.5 | 6.25 | 0.78 | 1.56 | 6.25 | 0.78 | 1.56 | 6.25 | 1.56 | 6.25 | 6.25 |
| 35 | — | — | 3.13 | — | 12.5 | 6.25 | 3.13 | 12.5 | 1.56 | 1.56 | 0.78 | 6.25 | 1.56 | 1.56 | 12.5 | 1.56 | — | 25 |
| 36 | — | 50 | 0.78 | — | 50 | 25 | 6.25 | 25 | 6.25 | 3.13 | 3.13 | 3.13 | 1.56 | 0.78 | 6.25 | 3.13 | — | 25 |
| 37 | — | 100 | 3.13 | — | 12.5 | 25 | 6.25 | 12.5 | 6.25 | 3.13 | 6.25 | 6.25 | 1.56 | 0.78 | 6.25 | 1.56 | 6.25 | 6.25 |
| 38 | — | 25 | 0.78 | — | 12.5 | 50 | 3.13 | 12.5 | 1.56 | 1.56 | 1.56 | 3.13 | 1.56 | 1.56 | 12.5 | 3.13 | — | 12.5 |

(1) *Proteus vulgaris* OXK US
(2) *Proteus vulgaris* OX 19US
(3) *Proteus mirabilis* IXM OM-19
(4) *Pseudomonas aeruginosa* ATCC 8689
(5) *Pseudomonas aeruginosa* 99 (Gentamycin resistant)
(6) *Psuedomonas ovalis* IMA 1002
(7) *Escherichia coli* kauffmann 0-1
(8) *Klebsiella pneumoniae* ATCC 10031
(9) *Salmonella typhi* H901 W
(10) *Salmonella enteritidis*
(11) *Shigella flexneri* 2a 1675
(12) *Shigella sonnei* II 37148
(13) *Bacillus megatherium* 10778
(14) *Bacillus subtilis* ATCC 6633
(15) *Micrococcus flavus* ATCC 10240
(16) *Staphylococcus aureus* 209P
(17) *Staphylococcus Shimanishi*
(18) *Staphylococcus Onuma*

An advantage of the compounds of this invention is that the salts, for example, sodium salts of these compounds are readily soluble in water at pH of living bodies, which makes them suitable for injections at high concentration. The solubility of these compounds are illustrated in Table 2 together with a control example.

Table 2

| Test sample (Exam. no.) | |
|---|---|
| 4 - b | The disodium salt of the compound was dissolved in water in an amount of more than 20% showing pH 7.4. |
| 6 | " |
| 13 | " |
| 16 | " |
| 23 | " |
| 24 | " |
| 25 | " |
| 26 - b | " |
| Control sample* | The sodium salt of the compound was dissolved clearly at 0.5%, the solution of the salt became slight turbid at 1%, became turbid at 5%, became thickly turbid at 10%, and was gelled at 20% |

*7-[D-α-4-hydroxynicotinoylamido-α-phenylacetamido]-3-(5-methyl-1,3,4-thiadiazol-2-yl)thiomethyl-Δ³-cephem-4-carboxylic acid Still another advantage of the compounds of this invention is that they are resistant to β-lactamase produced by gram negative bacteria.

For example, the relation between the amount (γ/ml) of an unaltered test sample at an initial concentration of the sample 100γ/ml against β-lactamase isolated from Pseudomonas aeruginosa 21 at various dilutions of the enzyme were investigated.

The results of the investigation are shown in Table 3.

Table 3

| Test sample | Dilution (magnification) of β-lactamase | | | | | | | | | |
|---|---|---|---|---|---|---|---|---|---|---|
| | ×2 | ×4 | ×8 | ×16 | ×32 | ×64 | ×128 | ×256 | ×512 | ×1024 |
| Compound of Example 4 - b | 0 | 29.6 | 61.0 | 100 | 100 | 100 | 100 | 100 | 100 | 100 |
| Cepalothin | 0 | 0 | 0 | 0 | 2.6 | 11.8 | 46.8 | 81.6 | 100 | 100 |
| Cefazolin | 0 | 0 | 0 | 0 | 0 | 9.2 | 21.5 | 84.6 | 96.7 | 100 |

Still another advantage of the compounds of this invention is that they are not inactivated in the internal organs of the body. For example, when the compounds of this invention and cephalotin are each homogenized with internal organs, the compounds of this invention are not decomposed while cephalotin is decomposed.

The relation between the reaction period of time and the antibacterial activity (residual activity, %) when these compounds are incubated with the plasma and the liver homogenate of a male Sprague-Dowley rat is shown in Table 4. The residual antibacterial activity was measured by a thin-layer cup method according to Bacillus subtilis ATCC 6633.

Table 4

| | A*(%) Time(minute) | | | | B*(%) Time(minute) | | | |
|---|---|---|---|---|---|---|---|---|
| | 0 | 15 | 30 | 90 | 0 | 15 | 30 | 90 |
| Compound of Example 4 | 100 | 97.0 | 93.9 | 103.0 | 100 | 93.5 | 91.3 | 102.2 |
| Compound of Example 6 | 100 | 92.0 | 102.0 | 102.0 | 100 | 95.7 | 89.1 | 91.3 |
| Compound of Example 9 | 100 | 103.0 | 92.0 | 100.0 | 100 | 100.0 | 100.0 | 102.5 |
| Cephalothin | 100 | 87.0 | 66.0 | 36.0 | 100 | 17.2 | 12.2 | 12.6 |
| Cephaloridine | 100 | 97.2 | 89.5 | 72.2 | 100 | 82.3 | 86.0 | 91.1 |

A*Residual activity (%) when incubated with 90% plasma.
B*Residual activity (%) when incubated with 10% liver homogenate.

The compounds of this invention are usually administered by an intravenous injection or an intramuscular injection, the dosage is ordinarily 1 g. per day per adult, and the amount can be increased up to 5 g. according to the condition of diseases and the patient. The dosage for a child is 20-40 mg./kg. and the amount can be increased up to 100 mg./kg. according to the condition of disease and the patent.

EXAMPLE 1-a

To 100 ml. of dichloromethane were added 4.2 g. of cephaloglycin monohydrate, 3.0 g. of anhydrous magnesium sulfate, and 2.1 ml. of triethylamine and after stirring the mixture for one hour at room temperature, magnesium sulfate was filtered off to provide a dichloromethane solution of cephaloglycin triethylamine salt. The solution was cooled to −30° C. and then 1.75 g. of 4-oxo-4H-thiopyran-3-carbonyl chloride and 2.1 ml. of triethylamine were added to the solution followed by stirring for one hour.

Then, the temperature of the mixture was returned to room temperature and after stirring for 1 hour, dichloromethane was distilled off under reduced pressure. Water was then added to the residue formed and after adjusting the pH thereof to 2 by adding dropwise 40% phosphoric acid to the mixture, the reaction mixture was extracted with 400 ml. of a mixture of butanol and ethyl acetate in 1 : 1 by volume ratio. The extract was washed with water, washed twice with a saturated aqueous sodium chloride solution, and after filtering off insoluble matters, the filtrate was dried over anhydrous magnesium sulfate. Then, when a butanol solution of 30% sodium 2-ethylhexanoate, precipitates formed, which was recovered by filtration, washed with ethyl acetate and ether, and then re-precipitated from a mixture of methanol and ether to provide 2.8 g. of sodium 7-D-[α-(4-oxo-4H-thiopyran-3-carbonylamino)-α-phenylacetamido]-cephalosporanate having a melting point of 185°-195° C. (decomp.).

Infrared absorption spectra: $\nu_{max}^{KBr}$ cm.$^{-1}$: 3450 (NH), 1770 (β-lactam), 1660 (amide), 1610 (carboxylate), and 1740 (ester).

Nuclear magnetic resonance spectra (D₆DMSO + CD₃OD). δ: 2.00 (3H, s, CH₃CO), 3.30 (2H, q(AB type),

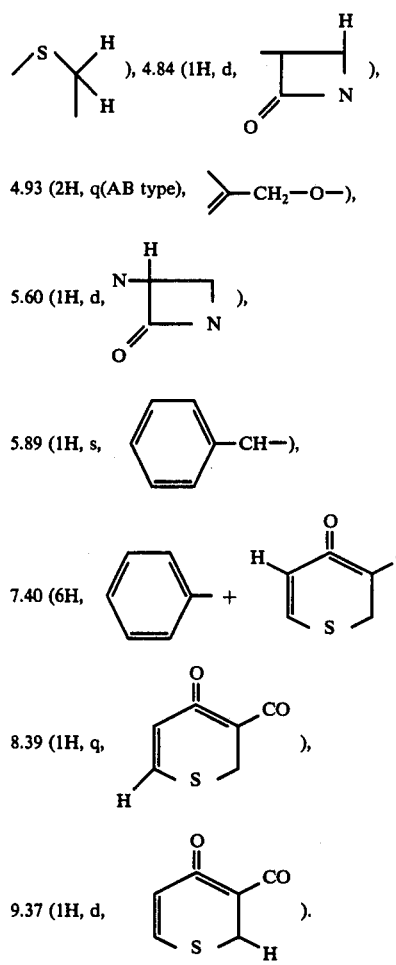

EXAMPLE 1-b

In 50 ml. of water were suspended 820 mg. of sodium 7-[D-α-(4-oxo-4H-thiopyran-3-ylcarboxamido)-α-phenylacetamido]cephalosporanate and 350 mg. of (5-mercapto-1,3,4-thiadiazol -2-yl)-succinamic acid and then after adding 3 ml of an aqueous 10% sodium dicarbonate to the suspension, the mixture was stirred for 23 hours while heating to 55° C. After the reaction was over, insoluble matters were filtered off from the reaction mixture and then the pH of the filtrate was adjusted to 2 by adding thereto 1 N hydrochloric acid. The precipitates formed were recovered by filtration, washed thoroughly with water, and then with ether, and dried over phosphorus pentoxide under reduced pressure. The product thus obtained was dissolved in 12 ml of dimethyl sulfoxide and after adding to the solution 0.9 ml of a 30% n-butanol solution of sodium 2-ethylhexanoate, the mixture was stirred for 5 minutes. Then, 120 ml of ethyl acetate was added to the reaction mixture and the resultant mixture was stirred for 10 minutes. The precipitates thus formed were recovered by filtration, washed thoroughly with ethyl acetate and then ether, and dried over phosphorus pentoxide under reduced pressure to provide 480 mg of the disodium salt of 7-[D-α-(4-oxo-4H-thiopyran-3-ylcarboxamido)-α-phenylacetamido]-3-[5-(3-carboxypropionylamino)-1,3,4-thiadiazol-2-yl]thiomethyl-Δ³-cephem-4-carboxylic acid.

Nuclear magnetic resonance spectra (D₂O): δ: 2.66 (4H, -NHCOC$\underline{H}_2$C$\underline{H}_2$CO₂Na).

Infrared absorption spectra: $v_{max}^{KBr}$ cm⁻¹: 1762 (β-lactam), 1660 (amide).

EXAMPLE 2-a

To a solution of 900 mg of cephaloglycin triethylamine salt and 17 ml of dichloromethane was added 550 mg of p-nitrophenyl 3-hydroxypyridazine-4-carboxylate under ice-cooling and then after adding 15 ml of dimethylformamide, the resultant mixture was stirred for 1 hour.

Then, the mixture was further stirred for 17 hours at room temperature. After the reaction was over, 23 ml. of dichloromethane was added to the reaction mixture and the mixture was extracted thrice with 40 ml. of an aqueous 1.5% sodium bicarbonate. The aqueous layer recovered was washed with dichloromethane, the pH of the aqueous solution was adjusted to 2 with 1 N hydrochloric acid, and then the precipitates formed were extracted with 60 ml. of a mixture of butanol and ethyl acetate in 1 : 1 by volume ratio. The extract was washed with water and then a saturated aqueous sodium chloride solution, and dried over anhydrous magnesium sulfate. To the solution was added 1.3 ml. of a 30% n-butanol solution of sodium 2-ethylhexanoate, the precipitates formed were recovered by filtration, washed with ethyl acetate and then ether, and dried over phosphorus pentoxide under reduced pressure to provide 600 mg. of sodium 7-D-α-(3-hydroxypyridazin -4-ylcarboxamido)-α-phenylacetamido]-cephalosporanate.

Nuclear magnetic resonance spectra (D₆-DMSO): δ: 8.16, 8.30 (hydrogen of the nucleus of pyridazine ring).

Infrared absorption spectra: $v_{max}^{KBr}$ cm⁻¹: 1760 (β-lactam), 1664 (amide).

EXAMPLE 2-b

In 25 ml. of water were suspended 400 mg. of sodium 7-D-α-(3-hydroxypyridazine-4-ylcarboxamido)-α-phenylacetamido]-cephalosporanate and 170 mg. of (5-mercapto-1,3,4-thiadiazol -2-yl)-succinamic acid and then 1.5 ml. of an aqueous 10% sodium bicarbonate solution was added to the suspension. The resultant mixture was stirred for 20 hours at 60° C. After the reaction was over, insoluble matters formed were filtered off from the reduction mixture and the pH of the filtrate was adjusted to 2 by adding thereto 1 N hydrochloric acid. The precipitates thus formed were recovered by filtration, washed thoroughly with water, 25 ml. of a mixture of methanol and ether in 1 : 5 by volume ratio, and then ether, and dried over phosphorus pentoxide under reduced pressure.

The product obtained was dissolved in 4 ml. of dimethyl sulfoxide, and after adding to the solution 0.5 ml. of a 30% n-butanol solution of sodium 2-ethylhexanoate, the resultant mixture was stirred for 5 minutes. To the reaction mixture was added 50 ml. of ethyl acetate and the mixture was stirred for 10 minutes. The precipitates thus formed were recovered by filtration, washed thoroughly with ethyl acetate and then ether, and dried over phosphorus pentoxide to provide 260 mg. of the disodium salt of 7-[D-α-(3-hydroxypyridazin -4-ylcarboxamido)-α-phenylacetamido]-3-{5-(3-carboxypropionylamino)-1,3,4-thiadiazol -2-yl}thiomethyl-Δ³-cephem-4-carboxylic acid.

Nuclear magnetic resonance spectra (D₂O): δ: 2.60 (4H-NHCOC$\underline{H}_2$CH₂CO₂Na)

Infrared absorption spectra: $\nu_{max}^{KBr}$ cm.$^{-1}$: 1762 ($\beta$-lactam), 1664 (amide).

EXAMPLE 3-a

After cooling a solution of 1.55 g. of cephaloglycin triethylamine salt and 25 ml. of dichloromethane to $-30°$ C., 0.60 g. of 2,4-dihydroxypyrimidine-5-carboxylic acid chloride and the mixture was stirred for 2 hours at temperatures of from $-20°$ C. to $-30°$ C. and then for 2 hours at room temperature. After the reaction was over, the reaction mixture was concentrated under reduced pressure and then 30 ml. of water was added to the concentrate. Then, the pH of the solution was adjusted to 2 by adding 1 N hydrochloric acid and then the precipitates formed were extracted with 120 ml. of a mixture of butanol and ethyl acetate in 1 : 1 by volume ratio.

The extract was washed with water and a saturated aqueous sodium chloride solution successively and dried over anhydrous magnesium sulfate and filtered. To the filtrate was added 1.8 ml. of a 30% n-butanol solution of sodium 2-ethylhexanoate and the precipitates formed were recovered by filtration, washed with ethyl acetate and then ether, and dried over phosphorus pentoxide under reduced pressure to provide 0.72 g. of sodium 7-[-D-$\alpha$-(2,4-dihydroxypyrimidin-5-ylcarboxamido)-$\alpha$-phenylacetamido]cephalosporanate.

Nuclear magnetic resonance spectra (D$_6$-DMSO): $\delta$: 8.28 (hydrogen of the nucleus of pyrimidine)

Infrared absorption spectra: $\nu_{max}^{KBr}$ cm.$^{-1}$: 1760 ($\beta$-lactam), 1676 (amide).

EXAMPLE 3-b

In 25 ml. of water were suspended 400 mg. of sodium 7-[D-$\alpha$-(2,4-dihydroxypyrimidin -5-ylcarboxamido)-$\alpha$-phenylacetamido]-cephalosporanate and 170 mg. of (5-mercapto-1,3,4-thiadiazol-2-yl)succinamic acid and after adding 1.5 ml. of an aqueous 10% sodium bicarbonate solution to the suspension, the mixture was stirred for 22 hours under heating to 55° C. After the reaction was over, insoluble matters formed were filtered off from the reaction mixture and the pH of the filtrate was adjusted to 2 by adding thereto 1 N hydrochloric acid. The precipitates formed were recovered by filtration, washed thoroughly with water and then ether, and dried over phosphorus pentoxide under reduced pressure. By treating the product as in Example 2-b, 220 mg. of the sodium salt of 7-[D-$\alpha$-(2,4-dihydroxypyrimidin-5-ylcarboxamido)-$\alpha$-phenylacetamido]-3-[5-(3-carboxypropionylamino)-1,3,4-thiadiazol -2-yl]thiomethyl-$\Delta^3$-cepham-4-carboxylic acid was obtained.

Nuclear magnetic resonance spectrum (D$_2$O) $\delta$: 2,62 (4H, -NHCOCH$_2$CH$_2$CO$_2$Na).

Infrared absorption spectra: $\nu_{max}^{KBr}$ cm.$^{-1}$: 1760 ($\beta$-lactam), 1664 (amide).

EXAMPLE 4-a

In 40 ml. of dichloromethane was suspended 1.4 g. of 4-hydroxynicotinic acid and after adding 1.4 ml. of triethylamine to the suspension, the mixture was stirred for 30 minutes at room temperature to form an almost transparent solution. The solution was cooled to 0°–5° C. and 10 ml. of dichloromethane containing 0.73 ml. of thionyl chloride was added dropwise to the solution at the same temperature. Thereafter, the mixture was stirred for 1 hour at room temperature to provide a suspension of 4-hydroxynicotinoyl chloride.

In 100 ml. of dichloromethane was suspended 4.25 g. of cephaloglycin monohydrate and then 2.8 ml. of triethylamine was dissolved therein. Furthermore, 5 g. of anhydrous magnesium sulfate was added to the system and after stirring the mixture for about 10 minutes at room temperature, the mixture was filtered to provide a solution of cephaloglycin triethylamine salt. The solution was cooled to $-20°$ C. and the suspension of 4-hydroxynicotinoyl chloride prepared above was added dropwise to the solution with stirring. Thereafter, the cooling bath was removed to raise the temperature up to room temperature and the mixture was stirred for about one hour at room temperature.

The reaction mixture obtained was concentrated at low temperature under reduced pressure and the solid residue formed was dissolved in 100 ml. of cold water. When the pH of the solution was adjusted to 2 with hydrochloric acid, white crystals were precipitated, which were recovered by filtration, washed with water and a small amount of acetone, and then dried.

The crystals thus recovered were dissolved in 30 ml. of dimethylformamide and insoluble matters formed were filtered off. Then, a n-butanol solution of 30% potassium 2-ethylhexanoate was added to the filtrate until the precipitation ceased. Furthermore, 100 ml. of ether was added to the suspension and after allowing to stand the mixture for a while, the precipitates were recovered by filtration and washed with acetone. Then, by purifying the precipitates by dissolving them in water-containing dimethylformamide followed by filtration and reprecipitating with the addition of acetone, 1.35 g. of potassium 7-D-[$\alpha$-(4-hydroxypyridine-3-carbonylamino)-$\alpha$-phenylacetamino]cephalosporanate was obtained as the yellowish brown powdery crystals. Melting point 195°–202° C. (decomp.)

Infrared absorption spectra: $\nu_{max}^{KBr}$cm.$^{-1}$: 3400 (NH, OH), 1760 ($\beta$-lactam), 1740 (acetate), 1655 (amide), 1600 (carboxylate).

Nuclear magnetic resonance spectra (CD$_3$OD + D$_6$-DMSO):

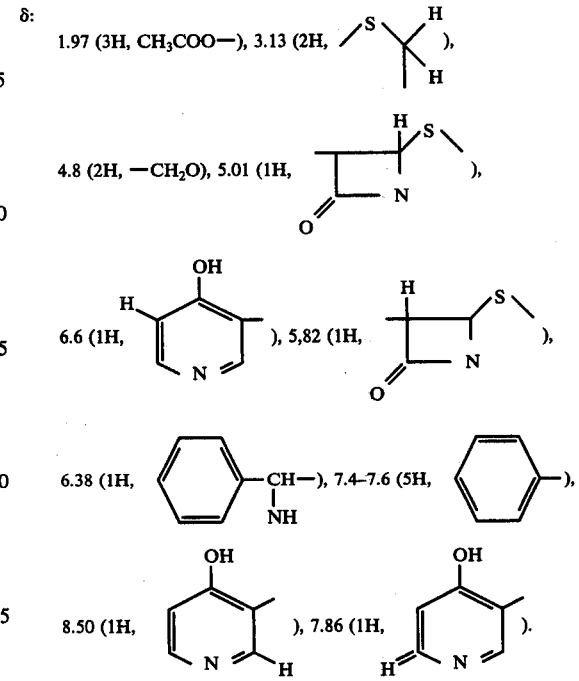

EXAMPLE 4-b

To 32 ml. of water were added 500 mg. of sodium 7-[D-α-(4-hydroxynicotinoylamido)-α-phenylacetamido]cephalosporanate, 209 mg. of (5-mercapto-1,3,4-thiadiazol-2-yl)thioacetic acid, and 203 mg. of sodium bicarbonate and the mixture was stirred for 22 hours at 55° C. Then, the pH of the reaction mixture was adjusted to about 2 by adding 1 N hydrochloric acid under ice-cooling and the white precipitates formed were recovered by filtration, washed thoroughly with water and then ether, and dried to provide 400 mg. of 7-[D-α-(4-hydroxynicotinoylamido)-α-phenylacetamido]-3-(5-carboxymethylthio-1,3,4-thiadiazol-2-yl)thiomethyl-Δ³-cephem-4-carboxylic acid.

Melting point about 250° C. (decomposed gradually).

Infrared absorption spectrum: $\nu_{max}^{KBr}$ cm.$^{-1}$: 1775 (β-lactam).

Nuclear magnetic resonance spectra (D$_6$-DMSO): δppm: 3,58 (2H), 4.13 (2H), 4.32 (2H), 5.02 (1H), 5.77 (1H), 5.79 (1H), 6.43 (1H), 7.36 (5H), 7.80 (1H), 8.43 (1H), and 9.42 (1H).

EXAMPLE 5

To 44 ml. of water were added 700 mg. of sodium 7-[D-α-(4-hydroxynicotinoylamido)-α-phenylacetamido]cephalosporanate, 312 mg. of 3-(5-mercapto-1,3,4-thiadiazol-2-ylthio)propionic acid, and 283 mg. of sodium bicarbonate and then the mixture was stirred for 2 hours at 55° C. Then, by treating the product as in Example 4-b, 520 mg. of 7-[D-α-(4-hydroxynicotinoylamido)-α-phenylacetamido]-3-(5-carboxyethylthio-1,3,4-thiadiazol-2-yl)-thiomethyl-Δ³-cephem-4-carboxylic acid was obtained.

Melting point about 250° C. (decomp.).

Infrared absorption spectrum: $\nu_{max}^{KBr}$ cm.$^{-1}$: 1775 (βlactam).

Nuclear magnetic resonance spectra (D$_6$-DMSO): δppm: 2.74 (2H), 3.42 (2H), 3.58 (2H), 4.32 (2H), 5.02 (1H), 5.77 (1H), 5.79 (1H), 6.43 (1H), 7.36 (5H), 7.80 (1H), 8.43 (1H), and 9.43 (1H).

EXAMPLE 6

To 40 ml. of water were added 615 mg. of sodium 7-[D-α-(4-hydroxynicotinoylamido)-α-phenylacetamido]-cephalosporanate, 235 mg. of 3-(5-mercapto-1,3,4-thiadiazol-2-yl)thiopropionic acid, and 218 mg. of sodium bicarbonate and the mixture was stirred for 2 hours at 55° C. Then, by treating the product as in Example 4-b, 450 mg. of 7-[D-α-(4-hydroxynicotinoylamido)-α-phenylacetamido]-3-(5-carboxyethyl-1,3,4-thiadiazol-2-yl)thiomethyl-Δ³-cephem-4-carboxylic acid was obtained.

Melting point about 250° C. (decomp.) Infrared absorption spectrum: $\nu_{max}^{KBr}$ cm.$^{-1}$: 1775 (β-lactam).

Nuclear magnetic resonance spectra (D$_6$-DMSO) δppm: 2.73 (2H), 3.25 (2H), 3.58 (2H), 4.35 (2H), 5.01 (1H), 5.78 (1H), 6.44 (1H), 7.36 (5H), 7.81 (1H), 8.44 (1H), 9.43 (1H).

EXAMPLE 7-a

To a suspension consisting of 4.23 g. of cephaloglycin monohydrate, 3.0 g. of anhydrous magnesium sulfate, and 70 ml. of methylene chloride are added 3.1 ml. of triethylamine and after stirring the mixture for one hour at room temperature, magnesium sulfate was filtered off to provide a triethylamine salt solution of cephaloglycin. To the solution was added dropwise a solution of nicotinoyl chloride N-oxide prepared by adding dropwise 0.73 ml. of thionyl chloride to a solution consisting of 1.39 g. of nicotinic acid N-oxide, 1.4 ml. of triethylamine, and 30 ml. of methylene chloride under ice-cooling followed by stirring for 1.5 hours. In this case, the pH of the reaction mixture was maintained at 8-9 by adding triethylamine.

Thereafter, the reaction mixture was stirred for 3 hours at a temperature of −20° + 5° C. and then allowed to stand overnight at −20° C. To the residue formed by distilling off n-butanol from the reaction mixture were added ice-water and a mixture of n-butanol and ethyl acetate in 2 : 3 by volume ratio and adjusted the pH thereof to 2.0 by the addition of dilute hydrochloric acid.

The organic layer formed was recovered, washed thrice with water, dried over anhydrous magnesium sulfate, and was mixed with a n-butanol solution of 30% sodium 2-ethylhaxanoate, whereby precipitates formed. By recovering the precipitates by filtration and re-precipitating them with a mixture of methanol and ether, 2.7 g. of sodium 7-[D-α-(pyridine-N-oxide-2-ylcarboxamid)-α-phenylacetamido] cephalosporanate was obtained.

Melting point about 263° C. (decomp.).

Infrared absorption spectra: $\nu_{max}^{KBr}$ cm.$^{-1}$: 3300 (NH), 1760 (β-lactam), 1735 (ester), 1665 (amide), and 1615 (carboxylate). Nuclear magnetic resonance spectra (D$_6$-DMSO):

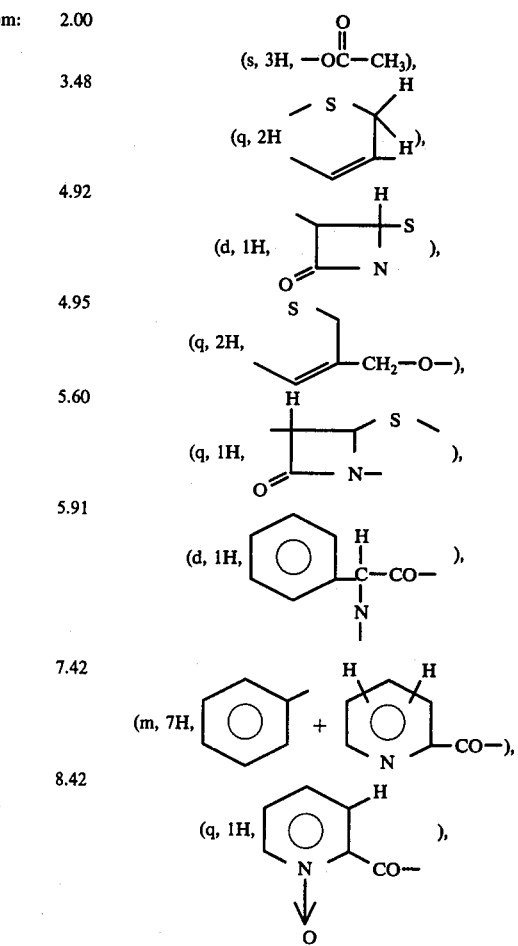

8.47 (q, 1N, 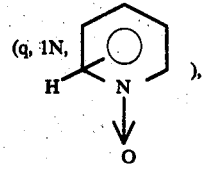 ), 9.46 (d, 1H, —NH), and 12.14 (d, 1H, —NH).

EXAMPLE 7-b

To a solution of 400 mg. of sodium 7-[D-α-(pyridine-N-oxide-2-ylcarboxamido)-α-phenylacetamido]cephalosporanate in 25 ml. of water was added 190 mg. of (5-mercapto-1,3,5-thiadiazol-2-yl)-succinamic acid at room temperature and further a saturated aqueous sodium bicarbonate solution was added to the mixture to adjust the pH of the solution to 6.8–7.2. The solution was stirred for 26 hours at 55°–60° C. and the pH thereof was then adjusted to 2.0 with diluted hydrochloric acid to form a suspension. The product thus obtained was extracted with a mixture of n-butanol and ethyl acetate in 2 : 3 by volume ratio and the organic layer formed was washed thrice with water, dried, and then mixed with a n-butanol solution of 30% sodium 2-ethylhexanoate and then ether to provide an oily material. The oily material thus obtained was dissolved in methanol and ether was added to the solution, whereby precipitates formed, which were recovered by filtration, washed with ether, and dried to provide 0.25 g. of sodium 7-[D-α-(pyridine-N-oxide-2-ylcarboxamido)-α-phenylacetamido]-3-[5-(3-carboxypropionylamino)-1,3,4-thiadiazol-2-yl]thiomethyl-Δ³-cephem-4-carboxylate.

Melting point about 251° C. (decomp).

Infrared absorption spectra: $\nu_{max}^{KBr}$ cm.$^{-1}$: 3300–3400 (broad, NH), 1760 (β-lactam), 1665 (amide), 1590 (carboxylate).

Nuclear magnetic resonance spectra (D₂O): δppm: 2.49 (m, 4H, —COCH₂CH₂—), 3.13 (q, 2H,

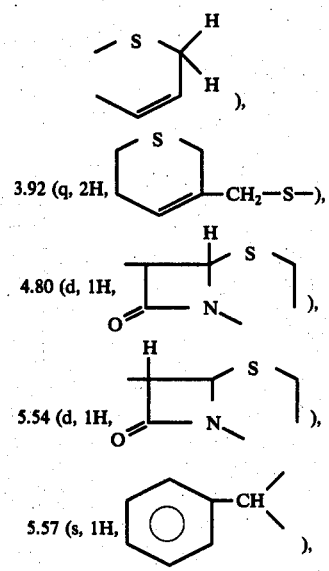

7.30 (m, 7H, 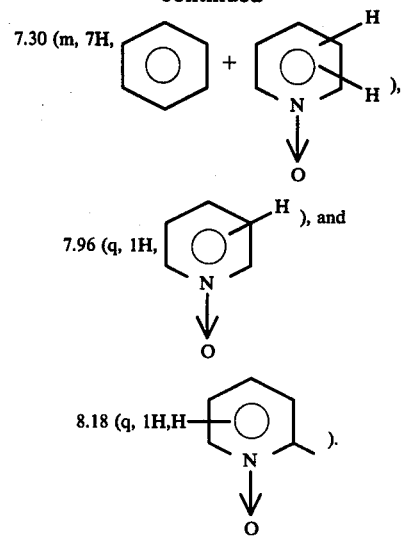

EXAMPLE 8-a

After stirring 35 ml. of a methylene chloride solution containing 2.12 g. of cephaloglycin monohydrate, 1.5 g. of anhydrous magnesium sulfate, and 1.4 ml. of triethylamine for one hour at room temperature, magnesium sulfate was filtered off to provide a solution of triethylamine salt of cephaloglycin. After cooling the solution to —25° C., 816 mg. of 2-imidazolidone-1-carboxylic acid chloride and further 0.3 ml. of triethylamine were added thereto.

The mixture thus obtained was stirred for 3 hours at —20° ± 5° C and then allowed to stand overnight at —20° C. Then, the solvent was distilled off from the reaction mixture under reduced pressure and the residue obtained was dissolved in ice water. The pH of the solution was adjusted to 2 with diluted hydrochloric acid and the precipitates formed were recoevered by filtration, washed with water, and dried to give 2.1 g. of the precipitates. The precipitates were dissolved in 20 ml. of dimethylformamide and then 3 ml. of a n-butanol solution of 30% sodium 2-ethylhexanoate was added to the solution. Then, ethyl acetate was addded to the mixture, whereby precipitates formed, which were recovered by filtration, washed with ether, and reprecipitated from a mixture of methanol and ether to provide 1.5 g. of sodium 7-[D-α-(2-imidazolidon -1-ylcarboxamido)-α-phenylacetamido]cephalosporanate.

Melting point about 225° C (decomp.)

Infrared absorption spectra: $\nu_{max}^{KBr}$ cm.$^{-1}$: 3100–3500 (NH), 1700 (β-lactam), 1720 (ester, $\geq$N—C(=O)—N$\leq$ ), 1660 (amide), and 1605 (carboxylate).

Nuclear magnetic resonance spectra (D₆-DMSO).

δ: 1.98 (s, 3H, —OCCH₃), 3.28 (q, 2H, 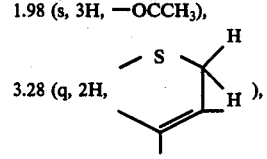 ),

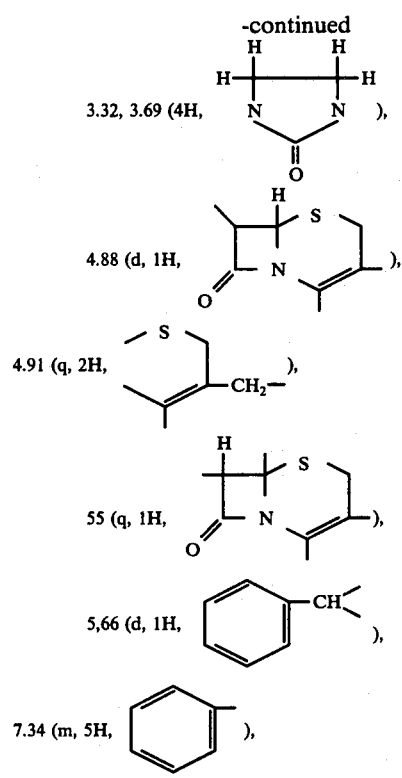

3.32, 3.69 (4H, ...), 4.88 (d, 1H, ...), 4.91 (q, 2H, ...), 55 (q, 1H, ...), 5,66 (d, 1H, ...), 7.34 (m, 5H, ...), 7.78 (1H, —NH), 9.13 (d, 1H, —NH), 9.35 (d, 1H, —NH).

EXAMPLE 8-b

To an aqueous solution of 800 mg. of sodium 7-[D-α-(2-oxoimidazolin-1-ylcarboxamido)-α-phenylacetamido]cephalosporanate in 50 ml. of water was added 0.38 g. of (5-mercapto-1,3,4-thiadiazol -2-yl)succinamic acid and then the pH of the solution was adjusted to 7.2–7.5 by adding a saturated sodium bicarbonate solution. The solution was stirred for 24 hours at 55°–60° C. and after cooling, the pH of the solution was adjusted to 2.0 by diluted hydrochloric acid whereby precipitates formed. The precipitates were recovered by filtration, washed with water, dried, and dissolved in 8 ml. of dimethylformamide. Then, 1 ml. of a n-butanol solution of 30% sodium 2-ethylhexanoate was added to the solution and then ethyl acetate was added thereto to form precipitates, which were recovered by filtration, washed with ether, and reprecipitated from a mixture of methanol and ether to provide 750 mg. of disodium 7-[D-α-(2-oxoimidazolin-1-ylcarboxamido)-α-phenylacetamido]-3-[5-(3-carboxypropionylamino)-1,3,4,-thiadiazol-2-yl]thiomethyl-Δ³-cephem-4-carboxylate.

Melting point: about 246° C. (decomp.)

Infrared absorption spectra: $\nu_{max}^{KBr}$ cm.$^{-1}$: 3200–3500 (NH), 1760 (β-lactam), 1720

(NHCNH), 1675, 1660 (amide), 1600 (carboxylate).

Nuclear magnetic resonance spectra (D$_2$O)

δppm: 2,56 (dd, 4H, —COCH$_2$CH$_2$COO—),

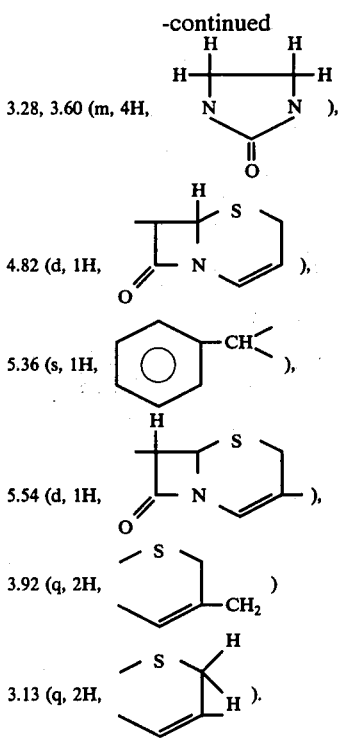

3.28, 3.60 (m, 4H, ...), 4.82 (d, 1H, ...), 5.36 (s, 1H, ...), 5.54 (d, 1H, ...), 3.92 (q, 2H, ...), 3.13 (q, 2H, ...).

EXAMPLE 9

To a mixture of 0.53 g. of sodium 7-[D-α-(4-hydroxynicotinoylamido)-α-phenylacetamido]cephalosporanate and 0.3 g. of sodium 5-mercapto-1,3,4-thiadiazol-2-yl-thioethylsulfonate were added 35 ml. of water and 0.108 g. of sodium bicarbonate and the resultant mixture was stirred for 22 hours at about 57° C. Then, after removing insoluble matters by filtration, the pH of the filtrate was adjusted to about 1 with 1.5 N hydrochloric acid under ice-cooling and the precipitates thus formed were recovered by filtration. The precipitates were washed with water and then ether and dried to give 0.45 g. of 7-[D-α-(4-hydroxynicotinoylamido)-α-phenylacetamido]-3-(5-sulfoethylthio-1,3,4-thiadiazol-2-yl)thiomethyl-Δ³-cephem-4-carboxylic acid.

Melting point: 200°–220° C. (gradually decomposed).

Infrared absorption spectrum: $\nu_{max}^{KBr}$ cm.$^{-1}$: 1774 (β-lactam).

Nuclear magnetic resonance spectra (D$_6$-DMSO):

δ(ppm): 1.89 (2H), 3.47 (2H), 3.59 (2H), 4.34 (2H), 5.05 (1H), 5.79 (1H), 5.87 (1H), 6.52 (1H), 7.41 (5H), 7.89 (1H), 8.49 (1H), and 9.47 (1H).

EXAMPLE 10

To 45 ml. of water were added 700 mg. of sodium 7-[D-α-(4-oxo-4H-thiopyran-3-ylcarboxamido)-α-phenylaceamido]cephalosporanate, 284 mg. of (5-mercapto-1,3,4-thiadiazol -2-yl)thioacetic acid, and 260 mg. of sodium bicarbonate and the resultant mixture was stirred for 20 hours at 50°–54° C. When the pH of the reaction mixture thus obtained was adjusted to about 2 with 1 N hydrochloric acid under ice-cooling and the precipitates formed were recovered by filtration, 530 mg. of the aimed product, 7-[D-α-(4-oxo-4H-thiopyran-3-ylcarboxamido)-α-phenylacetamido[-3-(5-carboxymethylthio-1,3,4-thiadiazole-2-yl)thiomethyl-Δ³-cephem-4-carboxylic acid was obtained.

Melting point about 190° C. (decomp.).

Infrared absorption spectrum:
$\nu_{max}^{KBr}$ cm.$^{-1}$: 1778 ($\beta$-lactam).

Nuclear magnetic resonance spectra (D$_6$-DMSO): $\delta$: 3.58 (2H), 4.14 (2H), 4.33 (2H), 5.02 (1H), 5.77 (2H), 7.35 (6H), 8.39 (1H), 9.34 (1H), and 9.48 (1H).

EXAMPLE 11

To 50 ml. of water were added 0.8 g. of sodium 7-[D-$\alpha$-(4-hydroxynicotinoylamido)-$\alpha$-phenylacetamido]-cephalosporanate, 0.281 b. of 5-mercapto-1,3,4-thiadiazol -2-carboxylic acid, and 0.296 g. of sodium bicarbonate and the resultant mixture was stirred for 20 hours at 55° C. Then, the pH of the reaction mixture thus obtained was adjusted to 1–2 with 1 N hydrochloric acid under ice-cooling and the white precipitates formed were recovered by filtration, washed with water, and dried to provide 0.5 g. of 7-[D-$\alpha$-(4-hydroxynicoytinoylamido)-$\alpha$-phenylacetamido]-3-(5-carboxy-1,3,4-thiadiazol -2-yl)thiomethyl-$\Delta^3$-cephem-4-carboxylic acid.

Infrared absorption spectrum: $\nu_{max}^{KBr}$ cm.$^{-1}$: 1770 ($\beta$-lactam).

Nuclear magnetic resonance spectra (D$_6$-DMS0): $\delta$ppm: 3,59 (2H, q), 4.39 (2H, 1), 5.02 (1H, d), 5.72 (1H), 5.84 (1H, d), 6.44 (1H, d), 7.37 (5H), 7.82 (1H, d), 8.45 (1H, s), 9.44 (1H, d), 11.23 (1H, d), 1220 (1H, broad).

EXAMPLE 12

To 70 ml. of water were added 700 mg. of 7-[D-$\alpha$-(7-methylthio-4-quinolone-3-carboxamido)-$\alpha$-phenylacetamido]cephalosporanic acid, 220 mg. of (5-mercapto-1,3,4-thiadiazol -2-yl)thioacetic acid, and 315 mg. of sodium bicarbonate, and the resultant mixture was stirred for 20 hours at 55°–60° C. After the reaction was over, the reaction mixture obtained was cooled, acidified with diluted hydrochloric acid, and the precipitates formed were recovered by filtration, washed well with water, and dried to provide 400 mg. of 7-[D-$\alpha$-(7-methylthio-4-quinolon -3-ylcarboxamido)-$\alpha$-phenylacetamido]-3-(5-carboxymethylthio-1,3,4-thiadiazol -2yl)thiomethyl-$\Delta^3$-cephem-4-carboxylic acid.

Infrared absorption spectrum: $\nu_{max}^{KBr}$ cm.$^{-1}$: 1780 ($\beta$-lactam).

Nuclear magnetic resonance spectra (D$_6$-DMSO): $\delta$ppm: 2.60 (3H), 3,56 (2H), 4.16 (2H), 4.20 (2H), 5.05 (1H), 5.84 (1H), 7.40 (7H), 8.18 (1H), 8.70 (1H), 9.50 (1H), 11.00 (1H), and 12.60 (1H).

EXAMPLE 13

In 50 ml. of water were suspended 0.80 g. of 7-[D-$\alpha$-(4-hydroxynicotinoylamido)-$\alpha$-phenylacetamido]cephalosporanic acid and 0.32 g. of (5-mercapto-1,2,4-thiadiazol-3-yl)thioacetic acid and after adding further 0.45 g. of sodium bicarbonate to the suspension, the mixture was stirred for 24 hours while heating to 55° C. After the reaction was over, insoluble matters were filtered off from the reaction mixture and the pH of the filtrate was adjusted to 2 by adding 5% hydrochloric acid to form precipitates, which were recovered by filtration, washed well with water and then dried over phosphorus pentoxide under reduced pressure to provide 0.70 g. of the powder of 7-[D-$\alpha$-(4-hydroxynicotinoylamido)-$\alpha$-phenylacetamido]-3-(3-carboxymethylthio-1,2,4-thiadiazol-5yl)thiomethyl-$\Delta^3$cephem-4-carboxylic acid.

Melting point: 189°–193° C. (decomp.)

Infrared absorption spectra: $\nu_{max}^{KBr}$ cm.$^{-1}$: 1770 ($\beta$-lactam) and 1650 (amide).

Nuclear magnetic resonance spectrum (D$_6$-DMSO): $\delta$ppm: 4.04 (2H, —SCH$_2$CO$_2$H)

EXAMPLE 14

To 50 ml. of water were added 0.8 g. of sodium 7-[D-$\alpha$-(4-hydroxynicotinoylamido)-$\alpha$-phenylacetamido]-cephalosporanate, 0.293 g. of 2-mercapto-4-methyl-thiazole-5-carboxylic acid, and 0.296 g of sodium bicarbonate and the resultant mixture was stirred for 22 hours at 55° C. Then, the pH of the reaction mixture was adjusted to 1–2 with 1 N hydrochloric acid under ice-cooling. The white precipitates thus formed were recovered by filtration, washed with water, and dried to provide 0.6 g of 7-[D-$\alpha$-(4-hydroxynicotinoylamido)-$\alpha$-phenylacetamido]-3-(4-methyl-5-carboxythiazol-2-yl)thiomethyl-$\Delta^3$-cephem-4-carboxylic acid.

Infrared absorption spectrum: $\nu_{max}^{KBr}$ cm.$^{-1}$: 1770 ($\beta$-lactam)

Nuclear magnetic resonance spectra (D$_6$-DMSO): $\delta$ppm: 2.56 (3H, s), 3.56 (2H, q), 4.37 (2H, q), 5.01 (1H, d), 5.74 (1H) 5.86 (1H, d), 6.44 (1H, d), 7.37 (5H), 7.82 (1H, d), 8.44 (1H, d), 9.44 (1H, d), 11.21 (1H, d), and 12,21 (1H, broad).

EXAMPLE 15

To 40 ml. of water were added 600 mg. of sodium 7-[D-$\alpha$-(4-hydroxynicotinoylamido)-$\alpha$-phenylacetamido] cephalo sporanate, 195 mg. of 5-mercapto-1-carboxymethyl tetrazole, and 180 mg. of sodium bicarbonate and the resultant mixture was stirred for 22 hours at 55° C. The reaction mixture thus obtained was filtered and the pH of the filtrate was adjusted to 1 with 1 N hydrochloric acid under ice-cooling. The precipitates formed were recovered by filtration, washed with water and then with ether, and dried to provide 300 mg. of 7-[D-$\alpha$-(4-hydroxynicotinoylamido)-$\alpha$-phenylacetamido]-3-(1-carboxymethyltetrazol-5-yl)-thiomethyl-$\Delta^3$-cephem-4-carboxylic acid.

Melting point: about 240° C (gradually decomposed)

Infrared absorption spectrum: $\nu_{max}^{KBr}$ cm.$^{-1}$: 1775 ($\beta$-lactam).

Nuclear magnetic resonance spectra (D$_6$-DMSO): $\delta$ppm: 3.60 (2H), 4.36 (2H), 5.00 (1H), 5.34 (2H), 5.84 (2H), 6.48 (1H), 7.44 (5H), 7.88 (1H), 8.50 (1H), 9.52 (1H).

EXAMPLE 16

To 30 ml. of water were added 0.45 g. of sodium 7-[D-$\alpha$-(4-hydroxynicotinoylamido)-$\alpha$-phenylacetamido]cephalosporanate, 0.2 g. of 6-carboxymethylthio-4-mercaptopyrimidine, and 0.14 g. of sodium bicarbonate and the resultant mixture was stirred for 22 hours at 55° C. After filtering the reaction mixture thus obtained, the pH of the filtrate was adjusted to 1 with 1 N hydrochloric acid under ice-cooling and the precipitates thus formed were recovered by filtration, washed with water and then ether, and dried to provide 0.42 g. of 7-]D-$\alpha$-(4-hydroxynicotionoylamido)-$\alpha$-phenylacetamido]-3-(6-carboxymethylthiopyrimidin -4-yl)thiomethyl-$\Delta^3$-cephem-4-carboxylic acid.

Infrared absorption spectrum: $\nu_{max}^{KBr}$ cm.$^{-1}$: 1775

Nuclear magnetic resonance spectra (D$_6$-DMSO): $\delta$ppm: 3.50 (2H), 3.98 (3H), 4.58 (1H), 5.00 (1), 5.74 (2H), 6.42 (1H), 7.34 (6H), 7.78 (1H), 8.42 (1H), 9.40 (1H).

EXAMPLE 17

To 37 ml. of water were added 0.5 g. of 7-[D-α-(4-hydroxynicotinoylamido)-α-phenylacetamido]cephalosporanic acid, 0.235 g. of 6-carboxymethylthio-4-mercapto-2-methylpyrimidine, and 0.295 g. of sodium bicarbonate and the resultant mixture was stirred for 22 hours at 50°-55° C. The reaction mixture thus obtained was filtered and the pH of the filtrate was adjusted to about 2 with 1 N hydrochloric acid under ice-cooling. The precipitates formed were recovered by filtration, washed with water and then ether, and dried under reduced pressure to provide 0.42 g. of 7-[D-α-(4-hydroxynicotinoylamido)-α-phenylacetamido]-3-(6-carboxymethylthio-2-methylpyrimidin-4-yl)thiomethyl-Δ³-cephem-4-carboxylic acid.

Infrared absorption spectrum: $\nu_{max}^{KBr}$ cm.$^{-1}$: 1778 (β-lactam).

Nuclear magnetic resonance spectra (D$_6$-DMSO): δppm: 2.50 (3H), 3.52 (2H), 3.82 (1H), 3.98 (2H), 4.62 (1H), 5.02 (1H), about 5.73 (1H), 5.85 (1H), 6.45 (1H), 7.23 (1H), 7.38 (5H), 7.82 (1H), 8.46 (1H), and 9.44 (1H).

EXAMPLE 18

To 37 ml. of water were added 526 mg. of 7-[D-α-(4-hydroxynicotinoylamido)-α-phenylacetamido]cephalosporanic acid, 220 mg. of 1-carboxymethyl-3-mercapto-6(1H)-pyridazinone, and 300 mg. of sodium bicarbonate and the resultant mixture was stirred for 22 hours at 50°-55° C. After the reaction was over, the reaction mixture obtained was filtered and the pH of the filtrate was then adjusted to about 2 with 1 N hydrochloric acid under ice-cooling. The precipitates thus formed were recovered by filtration, washed with water and then ether, and dried under reduced pressure to provide 350 mg. of 7-[D-α-(4-hydroxynicotinoylamido)-α-phenylacetamido]-3-(1-carboxymethyl-6(1H)-pyridazinon-3-yl)thiomethyl-Δ³-cephem-4-carboxylic acid.

Infrared absorption spectrum: $\nu_{max}^{KBr}$ cm.$^{-1}$: 1775 (β-lactam).

Nuclear magnetic resonance spectra (D$_6$-DMSO): δ(ppm): 3.46 (2H), 3.88 (1H), 4.33 (1H), 4.66 (2H), 4.93 (1H), 5.74 (2H), 6.40 (1H), 6.88 (1H), 7.34 (6H), 7.74 (1H), 8.40 (1H), and 9.41 (1H).

EXAMPLE 19

To 30 ml. of water were added 420 mg. of 7-[D-α-(4-hydroxynicotinoylamido)-α-phenylacetamido]cephalosporanic acid, 220 mg. of 2-amino-4-carboxymethylthio-6-mercaptopyrimidine, and 240 mg. of sodium bicarbonate and by treating the resultant mixture as in Example 18, 310 mg. of 7-[D-α-(4-hydroxynicotinoylamido)-α-phenylacetamido]-3-(2-amino-4-carboxymethylthiopyrimidin-6-yl)thiomethyl-Δ³-cephem-4-carboxylic acid was obtained.

Infrared absorption spectrum: $\nu_{max}^{KBr}$ cm.$^{-1}$: 1770

Nuclear magnetic resonance spectra (D$_6$-DMSO): δ(ppm): 3.52 (2H), 3.92 (3H), 4.46 (1H), 5.02 (1H), 5.76 (2H), 6.44 (2H), 6.68 (2H), 7.36 (5H), 7.82 (1H), 8.46 (1H), and 9.44 (1H).

EXAMPLE 20-a

To 20 ml. of methylene chloride were added 290 mg. of 4-hydroxy-2-methylpyrimidine-5-carboxylic acid and 0.3 ml of triethylamine and after cooling the resultant mixture to −10° C. with stirring, a solution of 148 mg. of ethyl chlorocarbonate in 3 ml. of methylene chloride was added dropwise to the mixture. The resultant mixture was stirred then for one hour at −10° C. and a solution of 500 mg. of cephaloglycin and 0.2 ml of triethylamine in 10ml. of methylene chloride was added to the mixture. The resultant mixture was further stirred for one hour at −10° C. and then for one hour at room temperature. After the reaction was over, the solvent was distilled off under reduced pressure and 5 ml. of water was added to the residue. After further adding thereto 30 ml. of a 1 : 1 mixture of n-butanol and ethyl acetate, the pH of the mixture was adjusted to 3 with 1 N hydrochloric acid followed by stirring well. Then, an organic solvent layer formed was recovered, washed with water and then a saturated aqueous sodium chloride solution, and then dried over anhydrous magnesium sulfate. The reaction mixture thus obtained was concentrated at room temperature and then 20 ml. of ether was added to the residue. The precipitates formed were recovered by filtration, washed with water and then ether, and dried under reduced pressure to provide 300 mg. of 7-[D-α-(4-hydroxy-2-methylpyrimidine-5-ylcarboxamide)-α-phenylacetamido]cephalosporanic acid.

Infrared absorption spectrum: $\nu_{max}^{KBr}$ cm.$^{-1}$: 1780 (β-lactam).

Nuclear magnetic resonance spectra (D$_6$-DMSO): δ(ppm): 2.00 (3H), 2,41 (3H), 3.41 (2H), 4.64 (1H), 4.95 (1H), 5.04 (1H), 5.80 (1H), 5.84 (1H), 7.39 (5H), 8.55 (1H).

EXAMPLE 20-b

In 18 ml. of water were dissolved 300 mg. of 7-[D-α-(4-hydroxy-2-methylpyrimidin -5-ylcarboxamido)-α-phenylacetamido]cephalosporanic acid, 112 mg. of 2-mercapto-1,3,4-thiadiazol -5-yl thioacetic acid, and 183 mg. of sodium bicarbonate and by treating the solution obtained as in Example 18, 240 mg. of 7-[D-α-(4-hydroxy-2-methylpyrimidin -5-ylcarboxamido)-α-phenylacetamido]-3-(5-carboxymethylthio-1,3,4-thiadiazol -2-yl)thiomethyl-Δ³-cephem-4-carboxylic acid was obtained.

Infrared absorption spectrum: $\nu_{max}^{KBr}$ cm.$^{-1}$: 1780 (β-lactam).

Nuclear magnetic resonance spectra (D$_6$-DMSO): δ(ppm): 2.36 (3H), 3.56 (2H), 4.12 (2H), 4.20 (1H), 4.50 (1H), 5.02 (1H), 5.72 (1H), 5.84 (1H), 7.38 (5H), and 8.60 (1H).

EXAMPLE 21

To a mixture of 0.5 g. of 7-[D-α-(4-hydroxynicotinoylamido)-α-phenylacetamido]cephalosporanic acid and 275 mg. of 2-(1-carboxyethylthio)-5-mercapto-1,3,4-thiadiazole were added 310 mg. of sodium bicarbonate and 37 ml. of water and the resultant mixture was stirred for 22 hours at 50°-55° C. Insoluble matters were filtered off from the reaction mixture thus obtained and the pH of the filtrate was adjusted to about 2 with 1 N hydrochloric acid under ice-cooling. The precipitates formed were recovered by filtration, washed with water and then ether, and dried under reduced pressure to provide 0.4 g. of 7-[D-α-(4-hydroxynicotinoylamido)-α-phenylacetamido]-3-[5-(1-carboxyethylthio)-1,3,4-thiadiazol-2-yl]thiomethyl-Δ³-cephem-4-carboxylic acid.

Infrared absorption spectrum: $\nu_{max}^{KBr}$ cm.$^{-1}$: 1778 (β-lactam).

Nuclear magnetic resonance spectra (D$_6$-DMSO): δ(ppm): 1.54 (3H), 3.58 (2H), 4.20 (1H), 4.37 (1H), 4.45

(1H), 5.02 (1H), about 5.76 (1H), 5.85 (1H), 7.39 (5H), 7.82 (1H), 8.45 (1H), and 9.45 (1H).

EXAMPLE 22

To a mixture of 500 mg. of 7-[D-α-(4-hydroxynicotinoylamido)-α-phenylacetamido]-cephalosporanic acid and 292 mg. of 2-(1-carboxy-1-methylethylthio)-5-mercapto-1,3,4-thiadiazole were added 320 mg. of sodium bicarbonate and 37 ml. of water and by treating the resultant mixture as in Example 21, 370 mg. of 7-[D-α-(4-hydroxynicotinoylamido)-α-phenylacetamido]-3-[5-(1-carboxy-1-methylethylthio)-1,3,4-thiadiazol-2-yl]thiomethyl-Δ³-cephem-4-carboxylic acid was obtained.

Infrared absorption spectrum: $\nu_{max}^{KBr}$ cm.$^{-1}$: 1777 (β-lactam).

Nuclear magnetic resonance spectra (D$_6$-DMSO): δ(ppm): 1.57 (6H), 3.59 (2H), 4.23 (1H), 4.45 (1H), 5.01 (1H), about 5.75 (1H), 5.84 (1H), 6.43 (1H), 7.37 (5H), 7.81 (1H), 8.43 (1H), and 9.42 (1H).

EXAMPLE 23

To 40 ml. of water were added 0.63 g. of 7-[D-α-(4-hydroxynicotinoylamido)-α-phenylacetamido]cephalosporanic acid, 0.25 g. of 2-mercapto-4-methylthiazole-5-acetic acid, and 0.3 g. of sodium bicarbonate and the resultant mixture was stirred for 1 hour at about 55° C. The pH of the reaction mixture thus obtained was adjusted to about 2 with 1 N hydrochloric acid under ice-cooling and the precipitates formed were recovered by filtration, washed with water, and dried to provide 0.55 g. of 7-[D-α-(4-hydroxynicotinoylamido)-α-phenylacetamido]-3-(5-carboxymethyl-4-methylthiazol-2-yl)thiomethyl-Δ³-cephem-4-carboxylic acid.

Infrared absorption spectrum: $\nu_{max}^{KBr}$ cm.$^{-1}$: 1772 (β-lactam).

Nuclear magnetic resonance spectra (D$_6$-DMSO): δ(ppm): 2.20 (3H), 3.53 (2H), 3.72 (2H), 4.02 (1H), 4.46 (1H), 4.97 (1H), 5.71 (1H), 5.82 (1H), 6.42 (1H), 7.33 (5H), 7.78 (1H), 8.40 (1H), 9.39 (1H), 11.15 (1H), and 12.02 (1H).

EXAMPLE 24

To 50 ml. of water were added 0.8 g. of sodium 7-[D-α-(4-hydroxynicotinoylamido)-α-phenylacetamido]-cephalosporanate, 0.386 g. of (2-mercapto-4-methylthiazol-5-yl)thioacetic acid, and 0.295 g. of sodium bicarbonate and the resultant mixture was stirred for 20 minutes at about 55° C. Then, the pH of the reaction mixture thus obtained was adjusted to about 2 with 1 N hydrochloric acid under ice-cooling and the precipitation formed were recovered by filtration, washed with water, and dried to provide 0.4 g. of 7-[D-α-(4-hydroxynicotinoylamido)-α-phenylacetamido]-3-(5-carboxymethylthio-4-methylthiazol-2-yl)thiomethyl-Δ³-cephem-4-carboxylic acid.

Infrared absorption spectrum: $\nu_{max}^{KBr}$ cm.$^{-1}$: 1768 (β-lactam).

Nuclear magnetic resonance spectra (D$_6$-DMSO): δ(ppm): 2.35 (3H), 3.50 (2H), 3.55 (2H), 4.07 (1H), 4.52 (1H), 4.99 (1H), 5.74 (1H), 5.84 (1H), 6.43 (1H), 7.34 (5H), 7.80 (1H), 8.43 (1H), 9.41 (1H), 11.29 (1H), and 12.16 (1H).

EXAMPLE 25

To 50 ml. of water were added 0.8 g. of sodium 7-[D-α-(4-hydroxynicotinoylamido)-α-phenylacetamido]-cepahlosporanate, 0.284 g. of 2-mercapto-1,3,4-thiadiazole-5-acetic acid, and 0.271 g. of sodium bicarbonate and the resultant mixture was stirred for 21 hours at 55° C. The pH of the reaction mixture thus obtained was adjusted to about 2 with 1 N hydrochloric acid under ice-cooling and the precipitates formed were recovered by filtration, washed with water, and dried to provide 0.45 g. of 7-[D-α-(4-hydroxynicotinoylamido)-α-phenylacetamido]-3-(5-carboxymethyl-1,3,4-thiadiazol -2-yl)thiomethyl-Δ³-cephem-4-carboxylic acid.

Infrared absorption spectrum: $\nu_{max}^{KBr}$ cm.$^{-1}$: 1774 (β-lactam).

Nuclear magnetic resonance spectra (D$_6$-DMSO): δ(ppm): 3.58 (2H), 3.17 (2H), 4.19 (1H), 4.53 (1H), 5.00 (1H), 5.71 (1H), 5.82 (1H), 6.42 (1H), 7.35 (5H), 7.79 (1H), 8.42 (1H), 9.43 (1H), 11.19 (1H), and 12.04 (1H).

EXAMPLE 26-a

In 150 ml. of methylene chloride was suspended 7.5 g. of cephaloglycin and after adding 5.0 g. of triethylamine and 5.0 g. of magnesium sulfate to the suspension, the resultant mixture was stirred for 30 minutes at room temperature. After the reaction was over, the reaction mixture was filtered and while cooling the filtrate to −30° C., 380 g. of 4-methoxynicotinic acid chloride was added all at once swoop to the filtrate followed by stirring for 2 hours at temperatures from −20° to −30° C. The reaction mixture was allowed to stand overnight at −8° C. and then stirred for 2 hours at room temperature. After the reaction was over, the solvent was distilled off at room temperature under reduced pressure from the reaction mixture, the residue formed was dissolved in 300 ml. of water. A small amount of insoluble matter present in the solution was filtered off and after adjusting the pH of the filtrate by adding an aqueous 5% hydrochloric acid solution, the filtrate was stirred for 30 minutes under ice-cooling. The precipitates thus formed were recovered by filtration, washed with water, an aqueous 1% hydrochloric acid solution, and then water sufficiently, and dried over phosphorus pentoxide under reduced pressure to provide 6.3 g. of the powder of 7-[D-α-(4-methoxynicotinoylamido)-α-phenylacetamido]-cephalosporanic acid.

Infrared absorption spectra: $\nu_{max}^{KBr}$ cm.$^{-1}$: 1774 (β-lactam), 1660 (acid amide), 1728 (acetate)

Nuclear magnetic resonance spectra (D$_6$-DMSO): δ(ppm): 3.74 (3H, —OMe), 6.42, 7.76, 8.42 (1H, 1H, 1H, the proton of pyridine nucleus), 2.00 (3H, —CH$_2$OCOC$\underline{H}_3$).

EXAMPLE 26-b

In 44 ml. of water were suspended 0.70 g. of 7-[D-α-(4-methoxynicotinoylamido)-α-phenylacetamido]cephalosporanic acid and 0.26 g. of 5-carboxymethylthio-2-mercapto-1,3,4-thiadiazole and after further adding 0.37 g. of sodium bicarbonate to the suspension, the resultant mixture was stirred for 22 hours at 55° C. After the reaction was over, a small amount of insoluble matters were filtered off from the reaction mixture and then the pH of the filtrate was adjusted to 1 by adding an aqueous 5% hydrochloric acid solution. The precipitates thus formed were recovered by filtration, washed well with water and then ether, and dried over phosphorus pentoxide under a reduced pressure to provide 0.76 g. of the white powder of 7-[D-α-(4-methoxynicotinoylamido)-α-phenylacetamido]-3-(5-carboxymethylthio-1,3,4-thiadiazole-2-yl)thiomethyl-Δ³-cephem-4-carboxylic acid.

Infrared absorption spectra: $\nu_{max}^{KBr}$ cm.$^{-1}$: 1770 ($\beta$-lactam), 1660 (acid amide).

Nuclear magnetic resonance spectra (D$_6$-DMSO): $\delta$(ppm): 3.76 (3H, —OMe), 3.56 (2H,

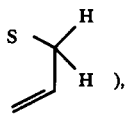

and 4.14 (2H, —S<u>CH$_2$</u>COOH).

EXAMPLE 27-a

To 18 ml. of dichloromethane were added 300 mg. of powder of 4-hydroxy-5-methylnicotinic acid and 230 mg. of triethylamine and the resultant mixture was stirred overnight at room temperature. To the resultant suspension was added 241 mg. of thionyl chloride under ice cooling, then stirred fro 30 minutes under ice cooling and further 1 hour at room temperature. The solvent was distilled off from the reaction mixture under a reduced pressure. A mixture of 500 mg. of cephaloglycin and 280 mg. of triethylamine, and 18 ml. of dichloromethane was cooled to $-20°$ C and was added to the white powdery residue thus formed followed by stirring for 2 hours at temperatures from $-10°$ to $-20°$ C. The mixture was allowed to stand overnight at the same temperature as above and then stirred for 2 hours at room temperature. The solvent was distilled off under a reduced pressure from the reaction mixture and then about 6 ml. of water was added to the residue formed. Insoluble precipitation (i. e., unchanged 4-hydroxy-5-methylnicotinic acid) were filtered off from the reaction mixture and the pH of the filtrate was adjusted to about 2 with 1 N hydrochloric acid under ice-cooling. The white precipitates thus formed were extracted with a 1 : 1 mixture of n-butanol and ethyl acetate and the extract was washed with water and then an aqueous saturated sodium chloride solution and dried with magnesium sulfate. After filtering off magnesium sulfate, a slightly excessive amount of a butanol solution of sodium 2-methylhexanoate and the precipitates formed were recovered by filtration, washed with ethyl acetate and ether, and dried to provide 400 mg. of 7-[D-α-(4-hydroxy-3-methylnicotinoylamido)-α-phenylacetamido]cephalosporanic acid.

Nuclear magnetic resonance spectra (D$_6$-DMSO): $\delta$(ppm): 1.91 (3H), 1.99 (3H), about 3.26 (2H), 4.70 (2H), 4.98 (1H), 5.73 (1H), 6.40 (1H), 7.24 (5H), 7.82 (1H), 8.28 (1H), and 9.34 (1H).

EXAMPLE 27-b

To 30 ml. of water were added 400 mg. of sodium 7-[D-α-(4-hydroxy-3-methylpyridin -5-ylcarboxamido)-α-phenylacetamido]-cephalosporanate, 193 mg. of 2-carboxymethylthio-5-mercapto-1,3,4-thiadiazole, and 172 mg. of sodium bicarbonate and the resultant mixture was stirred for 22 hours at 50°-53° C. Then, by treating the reaction mixture as in Example 21, 300 mg. of 7-[D-α-(4-hydroxy-3-methylpyridin -5-ylcarboxamido)-α-phenylacetamido]-3-(5-carboxymethylthio-1,3,4-thiadiazol-2-yl)thiomethyl-Δ$^3$-cephem-4-carboxylic acid.

Infrared absorption spectrum: $\nu_{max}^{KBr}$ cm.$^{-1}$: 1778 ($\beta$-lactam).

Nuclear magnetic resonance spectra (D$_6$-DMSO): $\delta$(ppm): 1.94 (3H), 3.55 (2H), 4.11 (2H), about 4.25 (2H), 5.00 (1H), 5.74 (2H), 7.34 (5H), 7.73 (1H), 8.34 (1H), and 9.38 (1H).

EXAMPLE 28-a

In 20 ml. of methylene chloride was suspended 0.50 g. of 6-hydroxy-4-methoxynicotinic acid and after adding 0.33 g. of triethylamine to the suspension, the mixture was stirred for 10 minutes. Then, after cooling the mixture to $-30°$ C., a solution of 0.40 g. of thionyl chloride in 6 ml. of methylene chloride was added dropwise to the mixture. Thereafter, the resultant mixture was stirred for one hour at $-25°$ C. Separately, 1.0 g. of cephaloglycin was suspended in 20 ml. of methylene chloride and after adding thereto 0.65 g. of triethylamine and then 1.0 g. of magnesium sulfate, the mixture was stirred for 20 minutes at room temperature. After the reaction was over, insoluble matters were filtered off from the reaction mixture, and after cooling the filtrate to $-45°$ C., the methylene chloride solution of the acid chloride cooled prepared above was added all at once to the filtrate.

Then, after stirring the mixture for 3 hours at temperatures from $-20°$ to $-30°$ C. and then for 1.5 hours at room temperature, the solvent was distilled off under reduced pressure and 30 ml. of water was added to the residue thus formed. The pH of the mixture was adjusted to 8 by adding an aqueous 5% sodium bicarbonate solution. Thereafter, the pH of the system was further adjusted to 2 by adding thereto an aqueous 5% hydrochloric acid solution and the precipitates formed were recovered by filtration, washed sufficiently with an aqueous 1% hydrochloric acid solution and then water, and dried over phosphorus pentoxide under reduced pressure to provide 0.80 g. of the white powder of 7-[D-α-(4-methoxy-6-hydroxynicotinoylamido)-α-phenylacetamido]cephalosporanic acid.

Infrared absorption spectra: $\nu_{max}^{KBr}$ cm.$^{-1}$: 1778 ($\beta$-lactam), 1662 (acid amide).

Nuclear magnetic resonance spectra (D$_6$-DMSO): $\delta$(ppm): 2.00 (3H), 3.40 (2H, 3H), 4.82 (2H), 5.04 (1H), 5.70 (1H), 5.78 (1H, 1H), 7.36 (5H), 8.42 (1H), 8.98 (1H), and 9.44 (1H).

EXAMPLE 28-b

In 43 ml. of water were suspended 0.69 g. of 7-[D-α-(6-hydroxy-4-methoxynicotinoylamido)-α-phenylacetamido]cephalosporanic acid and 0.28 g. of 2-carboxymethylthio-5-mercapto-1,3,4-thiadiazole and after adding 0.37 g. of sodium bicarbonate to the suspension, the resultant mixture was stirred for 23 hours at 55° C. After the reaction was over, a small amount of insoluble matters formed were filtered off from the reaction mixture and the pH of the filtrate was adjusted to 2 by adding an aqueous 5% hydrochloric acid solution. The precipitates formed were recovered by filtration, washed with water and then ether, and dried over phosphorus pentoxide under reduced pressure to provide 0.51 g. of the crystalline powder of 7-[D-α-(6-hydroxy-4-methoxynicotinoylamido)-α-phenylacetamido]-3-(5-carboxymethylthio-1,3,4-thiadiazol -2-yl)thiomethyl-Δ$^3$-cephem-4-carboxylic acid.

Infrared absorption spectra: $\nu_{max}^{KBr}$ cm$^{-1}$: 1778 ($\beta$-lactam) and 1664 (acid amide).

Nuclear magnetic resonance spectra (D$_6$-DMSO): $\delta$(ppm): 3.44 (2H, 3H), 4.14 (2H), 4.96 (2H), 5.04 (1H), 5.66 (1H), 5.76 (1H, 1H), 7.36 (5H), 8.40 (1H), 9.00 (1H), and 9.46 (1H).

EXAMPLE 29-a

To 30 ml. of methylene chloride were added 1 g. of cephaloglycin and 0.62 g. of triethylamine with stirring and after further adding 0.53 g. of 4-hydroxy-6-methylnicotinic acid chloride to the mixture at $-10°$ C., the resultant mixture was stirred for 4 hours at temperatures of from $-10°$ to $0°$ C. Thereafter, the reaction mixture was allowed to stand overnight at $-20°$ C. and after stirring the mixture for 3 hours at $10°-15°$ C., the solvent was distilled off from the reaction mixture under reduced pressure. Then, 30 ml. of water was added to the residue to dissolve the residue and after adjusting the pH of the solution to 1–2 by adding 1 N hydrochloric acid under ice-cooling, the product was extracted with a mixture of n-butanol and ethyl acetate in 1 : 1 by volume ratio. The extract was washed with water and then an aqueous saturated sodium chloride solution, and dried by anhydrous magnesium sulfate. Then, magnesium sulfate was filtered off from the system and the filtrate was mixed with a slight excess of a n-butanol solution of sodium 2-methylhexanoate with stirring. The precipitates thus formed were recovered by filtration and washed with ether to provide 0.4 g. of sodium 7-[D-$\alpha$-(4-hydroxy-6-methylnicotinoylamido)-$\alpha$-phenylacetamido]cepahlosporanate.

Nuclear magnetic resonance spectra (D$_6$-DMSO): (ddm): 1.91 (3H), 2.28 (3H), 3.14 (1H), 3.40 (1H), 4.71 (2H), 5.00 (1H), 5.76 (1H), 6.33 (1H), about 6.43 (1H), 7.23 (5H), 8.21 (1H), and 9.32 (1H).

EXAMPLE 29-b

To 20 ml. of water were added 250 mg. of 7-[D-$\alpha$-(4-hydroxy-6-methylnicotinoylamido)-$\alpha$-phenylacetamido]cepahlosporanic acid, 120 mg. of 2-mercapto-5-carboxymethylthio-1,3,4-thiadiazole, and 102 mg. of sodium bicarbonate and the resultant mixture was heated for 24 hours to $50°-53°$ C. with stirring. Then, the pH of the reaction mixture was adjusted to 1–2 with 1 N hydrochloric acid under ice-cooling and the precipitates formed were recovered by filtration, washed with water and then ether, and dried to provide about 170 mg. of 7-[D-$\alpha$-(4-hydroxy-6-methylnicotinoylamido)-$\alpha$-phenylacetamido]-3-(5-carboxymethylthio-1,3,4,-thiadiazol-2-yl)thiomethyl-$\Delta^3$-cephem-4-carboxylic acid.

Infrared absorption spectrum: $\nu_{max}^{KBr}$ cm$^{-1}$: 1776 ($\beta$-lactam).

Nuclear magnetic resonance spectra (D$_6$-DMSO): $\delta$(ppm): 2.26 (3H), 3.59 (2H), 4.15 (2H), 4.19 (1H), 4.50 (1H), 5.03 (1H), 5.79 (2H), 6.30 (1H), 7.39 (5H), 8.32 (1H), and 9.47 (1H).

EXAMPLE 30

In 47 ml. of water were suspended 0.75 g. of sodium 7-[D-$\alpha$-(4-hydroxynicotinoylamido)-$\alpha$-phenylacetamido]cephalosporanate and 0.29 g. of 1-amino-2-carboxymethylthio-5-mercapto-1,3,4-triazole and after adding further 0.29 g. of sodium bicarbonate to the suspension, the resultant mixture was stirred for 22 hours at $55°$ C. After the reaction was over, a small amount of insoluble matters in the mixture were filtered off and then the pH of the filtrate was adjusted to 2 by adding an aqueous 5% hydrochloric acid solution to the mixture. The precipitates thus formed were recovered by filtration, washed sufficiently with water and then ether, and dried over phosphorus pentoxide under reduced pressure to provide 0.62 g. of the crystalline powder of 7-[D-$\alpha$-(4-hydroxynicotinoylamido)-$\alpha$-phenylacetamido]-3-(1-amino-5-carboxymethylthio-1,3,4-triazol -2-yl)thiomethyl-$\Delta^3$-cephem-4-carboxylic acid.

Infrared absorption spectra: $\nu_{max}^{KBr}$ cm$^{-1}$: 1772 ($\beta$-lactam) and 1660 (acid amide).

Nuclear magnetic resonance spectra (D$_6$-DMSO). $\delta$(ppm): 3.58 (2H), 3.98 (2H), 5.04 (2H), 5.40 (2H), 5.70 (1H), 5.78 (1H), 5.82 (1H), 6.46 (1H), 7.36 (5H), 7.78 (1H), 8.46 (1H), 9.40 (1H, and 11.16 (1H).

EXAMPLE 31-a

To 10 ml. of chloroform were added 500 mg. of 7-(D-$\alpha$-amino-$\alpha$-p-hydroxyphenylacetamido) cephalosporanic acid trifluoroacetate and 190 mg. of triethylamine and after cooling the resultant mixture to $-20°$ C., 163 mg. of 4-thiopyrone-3-carboxylic acid chloride was added to the mixture with stirring. Then, after stirring the mixture for one hour at the same temperature as above and for 2 hours at room temperature, the solvent was distilled off from the reaction mixture under reduced pressure. To the residue thus formed was added 10 ml. of water and after acidifying the solution with 1 N hydrochloric acid, the product was extracted twice with 25 ml. of a 1 : 1 solution of n-butanol and ethyl acetate. The extract was washed with water and then dried and the solvent was distilled off under reduced pressure. Thereafter, ether was added to the residue thus formed and the precipitates formed were recovered by filtration to provide 380 mg. of 7-[D-$\alpha$-(4-thiopyrone-3-carboxamido)-$\alpha$-p-hydroxyphenyl- acetamido]cephalosporanic acid.

Infrared absorption spectrum: $\nu_{max}^{KBr}$ cm$^{-1}$: 1780 ($\beta$-lactam).

Nuclear magnetic resonance spectra (D$_6$-DMSO): $\delta$(ppm): 2.00 (3H), 3.40 (2H), 4.80 (2H), 5.02 (1H), 5.68 (2H), 6.70 (2H), 7.20 (2H), 7.22 (1H), 8.40 (1H), and 9.30 (1H).

EXAMPLE 31-b

To 10 ml. of water were added 150 mg. of 7-[D-$\alpha$-(4-thiopyrone- 3-carboxamido)-$\alpha$-p-hydroxyphenylacetamido]cephalosporanic acid, 61.5 mg. of 2carboxymethylthio-5-mercapto-1,3,4-thiadiazole, and 81.0 mg. of sodium bicarbonate and the mixture was stirred for 20 hours at $50°-55°$ C.

After the reaction was over, the reaction mixture thus obtained was acidified by adding 1 N hydrochloric acid under ice-cooling and the precipitates formed were recovered by filtration to provide 120 mg. of 7-[D-$\alpha$-(4-thiopyrone-3- carboxamido)-$\alpha$-p-hydroxyphenylacetamido]-3-[5-carboxymethylthio- 1,3,4-thiadiazol-2-yl]thiomethyl-$\Delta^3$-cephem-4-carboxylic acid.

Infrared absorption spectrum: $\nu_{max}^{KBr}$ cm$^{-1}$: 1770 ($\beta$-lactam).

Nuclear magnetic resonance spectra (D$_6$-DMSO): $\delta$(ppm): 3.56 (2H), 4.12 (2H), 4.30 (2H), .00 (1H), 5.64 (2H), 6.70 (2H), 7.10 (1H), 7.20 (2H), 8.36 (1H), and 9.30 (1H).

EXAMPLE 32

To 12 ml. of water were added 170 mg. of 7-[D-$\alpha$-(4-thiopyrone-3-carboxamido)-$\alpha$-p-hydroxyphenylacetamido]cephalosporanic acid, 87 mg. of 2-carboxymethyl-5-mercapto-1,3,4-thiadizole, and 92 mg, of sodium bicarbonate and the mixture was stirred for 15 hours at $50°-55°$ C. Then, by treating the mixture as in Example 31-b, 120 mg. of 7-[D-α-(4-thiopyrone-3-carboxamido)-α-p-hydroxyphenylacetamido]-3-[5-carboxymethyl-1,3,4-thiadiazol-2-yl]thiomethyl-Δ³-cephem-4-carboxylic acid was obtained.

Infrared absorption spectrum: $\nu_{max}^{KBr}$ cm$^{-1}$: 1775 (β-lactam).

Nuclear magnetic resonance spectra (D$_6$-DMSO): δ(ppm): 3.58 (2H), 4.16 (2H), 4.36 (2H), 5.00 (1H), 5.64 (2H), 6.70 (2H), 7.20 (2H), 7.22 (1H), 8.38 (1H), and 9.10 (1H).

EXAMPLE 33

To 10 ml. of water were added 150 mg of 7-[D-α-(4-hydroxynicotinoylamido)-α-p-hydroxyphenylacetamido]cephalosporanic acid, 63 mg. of 2-carboxymethylthio-5-mercapto-1,3,4-thiadiazole, and 83.3 mg. of sodium bicarbonate and the mixture was stirred for 20 hours at 50°-52° C. After the reaction was over, the reaction mixture was acidified by adding 1 N hydrochloric acid under ice-cooling and the precipitates formed were recovered by filtration to provide 60 mg. of 7-[D-α-(4-hydroxynicotinoylamido)-α-p-hydroxyphenylacetamido]-3-[5- carboxymethylthio-1,3,4-Δ³-thiadiazol-2-yl]thiomethyl-cephem-4-carboxylic acid.

Infrared absorption spectrum: $\nu_{max}^{KBr}$ cm$^{-1}$: 1770 (β-lactam).

Nuclear magnetic resonance spectra (D$_6$-DMSO): δ(ppm): 3.52 (2H), 4.08 (2H), 4.28 (2H), 4.64 (2H), 4.97 (1H), 6.36 (1H), 6.68 (2H), 7.20 (2H), 7.74 (1H), 8.39 (1H).

EXAMPLE 34

In 23 ml. of water were suspended 0.36 g. of sodium 7-[D-α- (4-hydroxynicotinoylamido)-α-phenylacetamido]cephalosporanate and 0.17 g. of 5-carboxymethylthio-2-mercapto-[1,2,4]-triazolo-[3,4-b]-[1,3,4]-thiadiazole and after adding 0.15 g. of sodium bicarbonate to the suspension, the resultant mixture was stirred for 26 hours at 55° C. After the reaction was over, insoluble matters formed were filtered off from the reaction mixture and then the pH of the filtrate was adjusted to 2 by adding aqueous 5% hydrochloric acid solution. Then, the precipitates thus formed were recovered by filtration, washed sufficiently with water and then ether, and dried over phosphorus pentoxide to provide 0.27 g. of the crystalline powder of 7-[D-α-(4-hydroxynicotinoyl-amido)-α-phenylacetamido]-3-(5-carboxymethylthio-[1,2,4]-triazolo-[3,4-b]-[1,3,4]-thiadiazol-2yl)thiomethyl-Δ³-cephem-4-carboxylic acid.

Infrared absorption spectra: $\nu_{max}^{KBr}$ cm$^{-1}$: 1776 (β-lactam) and 1660 (acid amide).

Nuclear magnetic resonance spectra (D$_6$-DMSO): δ(ppm): 3.56 (2H), 4.20 (2H), 4.96 (2H), 5.60 (1H), 5.76 (1H), 5.84 (1H), 6.42 (1H), 7.36 (5H), 7.80(1H), 9.42 (1H), 9.40 (1H), and 11.14 (1H).

EXAMPLE 35

To 20 ml. of water were added 300 mg. of sodium 7-[D-α-(4- hydroxynicotinoylamido)-α-phenylacetamido]cephalosporanate, 140 mg. of 4-(5-mercapto-1,3,4-thiadiazol-2-yl)butyric acid, and 120 mg. of sodium bicarbonate and the resultant mixture was stirred for 24 hours at 50°-52° C. Then, the pH of the reaction mixture was adjusted to about 2 with 1 N hydrochloric acid and the white precipitates thus formed were recovered and washed with water and then ether and dried to provide 200 mg. of 7-[D-α-(4-hydroxynicotinoylamido)-α- phenylacetamido]-3-[5-(3-carboxypropyl)-1,3,4-thiadiazol-2yl]- thiomethyl-Δ³cephem-4-carboxylic acid.

Infrared absorption spectrum: $\nu_{max}^{KBr}$ cm$^{-1}$-1780 (β-lactam).

Nuclear magnetic resonance spectra (D$_6$-DMSO): δppm: 1.91 (2H), 2.32 (2H), 3.06 (2H), 3.58 (2H), 4.17 (1H), 4.51 (1H), 5.01 (1H), 5.01 (1H), about 5.76 (1H), 5.84 (1H), 6.44 (1H), 7.38 (5H), 7.82 (1H), 8.45 (1H), and 9.47 (1H).

EXAMPLE 36

To 20 ml. of water were added 300 mg. of 7-[D-α-(4-hydroxy- 6-methylnicotinoylamido)-α-phenylacetamido]cephalosporanic acid, 142 mg. of 4-(5-mercapto-1,3,4-thiazol-2-yl)butyric acid, and 169 mg. of sodium bicarbonate and the mixture was stirred for 24 hours at 50°-52° C. Then, the pH of the reaction mixture was adjusted to about 2 with 1 N hydrochloric acid under ice-cooling and the precipitates formed were recovered by filtration, washed with water and then ether, and dried to provide 200 mg. of 7-[D-α-(4-hydroxy-6-methylnicotinoylamido)-α-phenylacetamido]-3-[5-(3-carboxypropyl)-1,3,4-thiadiazol-2-yl]thiomethyl-Δ³-cephem-4-carboxylic acid.

Infrared absorption spectrum: $\nu_{max}^{KBr}$ cm$^{-1}$: 1778 (β-lactam).

Nuclear magnetic resonance spectra (D$_6$-DMSO): δppm: 1.91 (2H), 2.25 (3H), 2.32 (2H), 3.06 (2H), 3.58 (2H), 4.18 (1H), 4.51 (1H), 5.00 (1H), about 5.75 (1H), 5.83 (1H), 6.29 (1H), 7.38 (5H), 8.32 (1H), and 9.46 (1H).

EXAMPLE 37 a. In 30 ml. of methylene chloride were added 500 mg. of 4-methoxy-6-methyl-nicotinic acid and 360 mg. of triethylamine and the mixture was cooled to −20° C with stirring. Then, 280 mg. of ethyl chlorocarbonate was added to the mixture and the resultant mixture was stirred for 2.5 hours at the same temperature.

After the reaction was over, the solution which was prepared by dissolving 1g. of cephaloglycin and 275 mg. of triethylamine in 20 ml. of methylene chloride was added to the reaction mixture, and then the resultant mixture was stirred for 2 hours at the temperature of −20° C. The reaction mixture was allowed to stand overnight at the same temperature and then stirred for 1 hour at the temperature of 0° C.

After the reaction was over, the solvent of the reaction mixture was distilled off under reduced pressure and the residue thus obtained was dissolved by adding about 40 ml. of water. The pH of the solution was adjusted with 1 N hydrochloric acid to 2 under ice-cooling, whereby precipitates were formed. The precipitates thus formed were recovered by filtration, washed with water and dried over, whereby 850 mg, of 7-[D-α-(4-methoxy-6-methyl-nicotinoylamido)-α-phenylacetamido]-cephalosporanic acid was obtained.

Infrared absorption spectra $\nu_{max}^{KBr}$ cm$^{-1}$: 1778 (62-lactam)

Nuclear magnetic resonance spectra (D$_6$-dimethylsulfoxide) δ(p.p.m.): 2.01 (3H), 2.32 (3H), 3.45 (2H), 3.72 (3H), 4.67 (1H), 4.99 (1H), 5.03 (1H), 5.81 (2H), 6.42 (1H), 7.38 (5H), 8.50 (1H), 9.50 (1H)

b. in 23 ml. of water were added 300 mg. of 7-[D-α-(4-methoxy- 6-methylnicotinoylamido)-α-phenylacetamido]-cephalosporanic acid, 140 mg. of 2-carboxymethylthio-5-mercapto-1,3,4-thiadiazole and 143 mg. of sodium bicarbonate, and the resultant mixture was allowed to stand for 24 hours at the temperature of 50° C.

After the reaction was over, the pH of the reaction mixture was adjusted to about 2 with 1 N hydrochloric acid under ice-cooling, whereby precipitates were formed. The precipitates thus formed were recovered by filtration, washed with water and then with ether and dried over, whereby 250 mg. of 7[-α-(4-methoxy-6-methylnicotinoylamido)-α-phenylacetamido]-3-(5-carboxymethyl- thio-1,3,4-thiadiazol-2yl)-thiomethyl-Δ³-cephem-4-carboxylic acid was obtained.

Infrared absorption spectra $\nu_{max}^{KBr}$cm$^{-1}$: 1778 (β-lactam)

Nuclear magnetic resonance spectra (D$_6$-dimethylsufoxide) δ(p.p.m.): 2.54 (3H), 3.60 (2H), 3.74 (3H), 4.18 (2H), 4.21 (1H), 4.52 (1H), 5.05 (1H), 5.83 (2H), 6.45 (1H), 7.43 (5H), 8.52 (1H), 9.53 (1H)

EXAMPLE 38

In 20 ml. of water were added 300 mg. of 7-[D-α-(4-hydroxy- 6-methylnicotinoylamido)-α-phenylacetamido]-cephalosporanic acid, 127 mg. of 2-carboxymethyl-5-mercapto-1,3,4-thiadiazole and 174 mg. of sodium bicarbonate, and the resultant mixture was allowed to stand for 22 hours at the temperature of 50° C.

After the reaction was over, the insoluble matter in the reaction mixture was filtered off and the pH of the filtrate was adjusted to about 2 with 1 N hydrochloric acid under ice-cooling and then the product was extracted with a mixture of n-butanol and ethyl acetate (1 : 1 in volume ratio). The extract was washed with saturated aqueous solution of sodium chloride and then dried over anhydrous magnesium sulfate. Then, slightly excessive amount of sodium 2-methylhexanate was added to the solution, whereby precipitates were formed. The precipitates thus formed were recovered by filtration, washed with water and then with ether and dried over, whereby 250mg. of sodium salt of 7-[D-α-(4-hydroxy-6- methylnicotinoylamido)-α-phenylacetamido]-3-(5-carboxymethyl- 1,3,4-thiadiazol-2-yl)-thiomethyl-Δ³-cephem-4-carboxylic acid was obtained.

Infrared absorption spectra $\nu_{max}^{KBr}$cm$^{-1}$: 1765 (β-lactam)

Nuclear magnetic resonance spectra (D$_6$-dimethylsulfoxide) δ(p.p.m.): 2.28 (3H), 3.47 (2H), 3.66 (2H), 4.14 (1H), 4.50 (1H), 4.93 (1H), 5.65 (1H), 6.16 (1H), 6.28 (1H), 7.27 (5H), 8.27 (1H), 9.34 (1H)

What is claimed is:
1. Cephalosporin compounds of the formula:

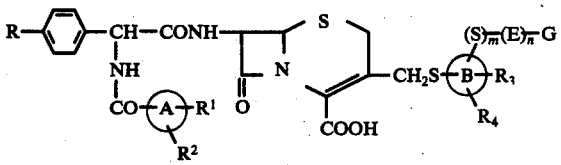

wherein R is hydrogen or hydroxy;

Ⓐ is an aromatic heterocyclic ring selected from the group consisting of pyridine, pyrimidine, pyridazine, pyrazine, and thiopyran; R¹ and R² which may be the same or different are each hydrogen, hydroxy, lower alkyl, lower alkoxy, lower alkylthio, or oxo;

Ⓑ is thiazole, thiadiazole, tetrazole, pyrimidine, pyridazine or 1,2,4-triazolo (3,4-b)-1,3,4-thiadiazole;

R³ and R⁴ when they are present which may be the same or different are hydrogen, amino, oxo, or lower alkyl;

E. is alkylene; G is carboxy or sulfo;

n is 0 or 1 when m is 0; and n is 1 when m is 1 and the pharmaceutically acceptable salts thereof.

2. The cephalosporin compound and pharmaceutically acceptable salt thereof as claimed in claim 1 wherein said ring Ⓐ is a pyridine ring and said ring Ⓑ is a 1,3,4-thiadiazole ring.

3. The cephalosporin compound and the pharmaceutically acceptable salts thereof as claimed in claim 1 wherein said ring Ⓐ is a pyridine ring and said ring Ⓑ is a 1,2,4-thiadiazole ring.

4. The cephalosporin compound and the pharmaceutically acceptable salts thereof as claimed in claim 1 wherein said ring Ⓐ is a pyridine ring and said ring Ⓑ is a thiazole ring.

5. 7-[D-α-(4-hydroxynicotinoylamido)-α-phenylacetamido]-3-(5-carboxymethylthio-1,3,4-thiadiazol-2-yl)thiomethyl-Δ³-cephem-4-carboxylic acid and the pharmaceutically acceptable salts thereof.

6. 7-[D-α-(4-hydroxynicotinoylamido)-α-phenylacetamido]-3-(3-carboxymethylthio-1,2,4-thiadiazol-5-yl)thiomethyl-Δ³-cephem-4-carboxylic acid and a pharmaceutically acceptable salt thereof.

7. 7-[D-α-(4-hydroxynicotinoylamido)-α-phenylacetamido]-3-(5-carboxymethylthio-4-methylthiazol-2-yl)-thiomethyl-Δ³-cephem-4-carboxylic acid and a pharmaceutically acceptable salt thereof.

8. 7-[D-α-(4-hydroxynicotinoylamido)-α-phenylacetamido]-3-(5-carboxymethyl-1,3,4-thiadiazol-2-yl)-thiomethyl-Δ³-cephem-4-carboxylic acid and a pharmaceutically acceptable salt thereof.

9. 7-[D-α-(4-hydroxy-3-methylnicotinoylamido)-α-phenylacetamido]-3-(5-carboxymethylthio-1,3,4-thiadiazol-2-yl)thiomethyl-Δ³-cephem-4-carboxylic acid and a pharmaceutically acceptable salt thereof.

10. 7-[D-α-(4-hydroxy-6-methylnicotinoylamido)-α-phenylacetamido]-3-(5-carboxymethylthio-1,3,4-thiadiazol-2-yl)thiomethyl-Δ³-cephem-4-carboxylic acid and a pharmaceutically acceptable salt thereof.

11. A cephalosporin compound according to claim 1 which is 7-[D-α-(4-hydroxynicotinoylamido)-α-phenylacetamido]-3-(5-carboxy-4-methylthiazol-2-yl)thiomethyl-Δ³-cephem-4-carboxylic acid and the pharmaceutically acceptable salts thereof.

12. A cephalosporin compound according to claim 1 which is 7-[D-α-(4-hydroxynicotinoylamido)-α-phenylacetamido]-3-(1-carboxymethyltetrazol-5-yl)thiomethyl-Δ³-cephem-4-carboxylic acid and the pharmaceutically acceptable salts thereof.

13. A cephalosporin compound according to claim 1 which is 7-[D-α-(4-hydroxynicotinoylamido)-α-phenylacetamido]-3-(5-(2-sulfoethylthio)-1,3,4-thiadiazol-2-yl)thiomethyl-Δ³-cephem-4- carboxylic acid and the pharmaceutically acceptable salts thereof.

14. A cephalosporin compound according to claim 1 which is 7-[D-α-(4-oxo-4H-thiopyran-3-ylcarboxamido)-α-phenylacetamido]- 3-(5-carboxymethylthio-1,3,4-thiadiazol-2-yl)thiomethyl-Δ³-cephem- 4-carboxylic acid and the pharmaceutically acceptable salts thereof.

15. A cephalosporin compound according to claim 1 which is 7[D-α-(4-hydroxynicotinoylamido)-α-phenylacetamido]-3-(5-carboxymethyl-4-methylthiazol-2-yl)thiomethyl-Δ³-cephem-4-carboxylic acid and the pharmaceutically acceptable salts thereof.

* * * * *